United States Patent
Lochmann et al.

(10) Patent No.: US 11,919,851 B2
(45) Date of Patent: Mar. 5, 2024

(54) METHOD FOR PRODUCING POLYOL-BASED ESTERS OF OPTIONALLY ACYLATED HYDROXYCARBOXYLIC ACIDS

(71) Applicant: IOI Oleo GmbH, Witten (DE)

(72) Inventors: Dirk Lochmann, Witten (DE); Sebastian Reyer, Witten (DE); Michael Stehr, Witten (DE)

(73) Assignee: KETOLIPIX THERAPEUTICS GMBH (DE)

( * ) Notice: Subject to any disclaimer, the term of this patent is extended or adjusted under 35 U.S.C. 154(b) by 124 days.

(21) Appl. No.: 17/379,204

(22) PCT Filed: Jan. 23, 2019

(86) PCT No.: PCT/EP2019/051547
§ 371 (c)(1),
(2) Date: Jul. 19, 2021

(87) PCT Pub. No.: WO2020/147983
PCT Pub. Date: Jul. 23, 2020

(65) Prior Publication Data
US 2023/0150915 A1    May 18, 2023

(30) Foreign Application Priority Data
Jan. 17, 2019  (WO) ................ PCT/EP2019/051127

(51) Int. Cl.
| | |
|---|---|
| *C07C 67/08* | (2006.01) |
| *A23L 33/10* | (2016.01) |
| *A61K 31/22* | (2006.01) |
| *C07C 69/675* | (2006.01) |

(52) U.S. Cl.
CPC ............ *C07C 69/675* (2013.01); *A23L 33/10* (2016.08); *A61K 31/22* (2013.01); *C07C 67/08* (2013.01)

(58) Field of Classification Search
CPC .............................. C07C 67/08; C07C 69/675
See application file for complete search history.

(56) References Cited

U.S. PATENT DOCUMENTS

| | | | | |
|---|---|---|---|---|
| 5,519,161 A | * | 5/1996 | Birkhahn | .............. C07C 69/675 560/185 |
| 2015/0164855 A1 | * | 6/2015 | Clarke | .................... A61P 21/00 514/460 |

FOREIGN PATENT DOCUMENTS

| | | | | |
|---|---|---|---|---|
| WO | 9509145 | | 4/1995 | |
| WO | WO-9509145 A1 | * | 4/1995 | ........... C07C 69/675 |
| WO | 2013150153 | | 10/2013 | |
| WO | WO-2013150153 A1 | * | 10/2013 | ............. A61K 31/22 |

* cited by examiner

*Primary Examiner* — Yate' K Cutliff
(74) *Attorney, Agent, or Firm* — Edward E. Sowers; Brannon Sowers & Cracraft PC

(57) ABSTRACT

The invention relates to a method for producing polyol esters, especially polyglycerol esters, of optionally acylated 3-hydroxybutyric acid, as well as the products thus obtained and their use.

19 Claims, No Drawings

METHOD FOR PRODUCING POLYOL-BASED ESTERS OF OPTIONALLY ACYLATED HYDROXYCARBOXYLIC ACIDS

CROSS-REFERENCES TO RELATED APPLICATIONS

This application is a National Stage filing of International Application PCT/EP 2019/051547 filed Jan. 23, 2019, entitled "METHOD FOR PRODUCING POLYOL-BASED ESTERS OF OPTIONALLY ACYLATED HYDROXY CABOXYLIC ACIDS", claiming priority to PCT/EP 2019/051127, filed Jan. 17, 2019. The subject application claims priority to PCT/EP 2019/051547 and PCT/EP 2019/051127, and incorporates all by reference herein, in their entirety.

BACKGROUND OF THE INVENTION

The present invention relates to the field of keto bodies and related metabolism and the therapy of related diseases.

Especially, the present invention relates to a method for producing polyol esters of optionally acylated 3-hydroxybutyric acid, especially polyglycerol esters of optionally acylated 3-hydroxybutyric acid, as well as the reaction products thus obtainable or thus prepared (i.e. polyol esters of optionally acylated 3-hydroxybutyric acid, especially polyglycerol esters of optionally acylated 3-hydroxybutyric acid) and their use, especially in pharmaceutical compositions, such as drugs or medicaments, or in food and/or food products, as well as their further applications or uses.

Furthermore, the present invention relates to pharmaceutical compositions, especially drugs or medicaments, comprising the reaction products (i.e. polyol esters of optionally acylated 3-hydroxybutyric acid, especially polyglycerol esters of optionally acylated 3-hydroxybutyric acid) obtainable or produced according to the inventive method, as well as their applications or uses.

Finally, the present invention relates to food and/or food products, especially food supplements, functional foods, novel foods, food additives, food supplements, dietary foods, power snacks, appetite suppressants and strength and/or endurance sports supplements, which comprise the reaction products (i.e. polyol esters especially polyglycerol esters, of optionally acylated 3-hydroxybutyric acid) obtainable or produced according to the inventive method, as well as their applications or uses.

The term optionally acylated 3-hydroxybutyric acid, as used according to the invention, refers especially to a 3-hydroxybutyric acid which 3-hydroxy function is optionally acylated, especially acetylated or propionylated, preferentially acetylated (i.e. the hydrogen atom of the 3-hydroxyl function of the 3-hydroxybutyric acid is optionally replaced by an acyl group, i.e. a group —C(O)—R with R=alkyl, especially by an acetyl group —C(O)—CH$_3$ or propionyl group —C(O)—C$_2$H$_5$, preferentially by an acetyl group —C(O)—CH$_3$); consequently, the same applies to the relevant carboxylic acid anhydride of 3-hydroxybutyric acid, i.e. its acylated form. Consequently, the reaction products according to the invention (i.e. polyol esters of optionally acylated 3-hydroxybutyric acid, especially polyglycerol esters of optionally acylated 3-hydroxybutyric acid) optionally exhibit the relevant acylation in the 3-position of the 3-hydroxybutyric acid residue or moiety in the respective ester; in other words, for example, a polyol ester of acylated 3-hydroxybutyric is synonymous with a polyol ester of 3-acyloxybutyric acid etc. (For example, a polyol ester of acetylated 3-hydroxybutyric acid is synonymous with a polyol ester of 3-acetoxybutyric acid, etc.).

In the human energy metabolism, glucose is the short-term available energy carrier, which is metabolized into energy in the mitochondria by releasing water and carbon dioxide. The glycogen stores of the liver are already emptied during the sleep period during the night. However, especially the human central nervous system (CNS) and the heart require a permanent energy supply.

The physiological alternative to glucose, which is mainly available to the central nervous system, are the so-called keto bodies (synonymously also called ketone bodies).

The term keto body is especially a collective term for three compounds, which are formed mainly in catabolic metabolic states (such as hunger, reduction diets or low-carbohydrate diets) and may lead to ketosis. The term keto bodies includes especially the three compounds acetoacetate (synonymously also referred to as acetacetate) and acetone as well as 3-hydroxybutyric acid (hereinafter also synonymously referred to as beta-hydroxybutyric acid or BHB or 3-BHB) or its salt (i.e. 3-hydroxybutyrate or beta-hydroxybutyrate), the latter being the most important of the three aforementioned compounds. 3-Hydroxybutyric acid or its salt occurs physiologically as the (R)-enantiomer, i.e. as (R)-3-hydroxybutyric acid (synonymously also called (3R)-3-hydroxybutyric acid to emphasize the center of chirality in the 3-position) or its salt.

These keto bodies are also provided physiologically in large amounts from lipids stored in the body by lipolysis during fasting or starvation and replace the energy source glucose almost completely.

The keto bodies are formed in the liver from acetyl coenzyme A (=acetyl-CoA), which originates from beta-oxidation; they represent a transportable form of the acetyl coenzyme A in the human body. However, in order to utilize the keto bodies, the brain and muscles must first adapt by expressing enzymes that are required to convert keto bodies back into acetyl coenzyme A. Especially in times of hunger, the keto bodies contribute a considerable amount to energy production. For example, after some time the brain is able to get by with only a third of the daily amount of glucose.

Physiologically, the keto bodies are synthesized from two molecules of activated acetic acid in the form of acetyl coenzyme A, the normal intermediate product of fatty acid degradation, which is extended using a further acetyl coenzyme A unit and the enzyme HMG-CoA-synthase to the intermediate product 3-hydroxy-3-methyl-glutaryl-CoA (HMG-CoA), wherein finally the HMG-CoA-lyase cleaves off the acetoacetate. These three steps take place exclusively in the mitochondria of the liver (lynen cycle), wherein 3-hydroxybutyrate is finally formed in the cytosol by the D-beta-hydroxybutyrate dehydrogenase. HMG-CoA is also an end product of the degradation of the amino acid leucine, while acetoacetate is formed during the degradation of the amino acids phenylalanine and tyrosine.

Spontaneous decarboxylation turns acetoacetate into acetone; it can occasionally be perceived in the breath of diabetics and dieters. It cannot be further used by the body. However, the proportion of acetone in the keto bodies is small.

Acetoacetate is thus reductively converted into the physiologically relevant form of 3-hydroxybutyric add or 3-hydroxybutyrate, but can also decompose into the physiologically unusable acetone with the release of carbon dioxide, which is detectable and olfactory perceptible in severe ketosis, a ketoacidosis (e. g. in diabetes mellitus type 1 patients without insulin substitution), in the urine and in the exhaled air.

3-Hydroxybutyric acid is currently used and marketed in the weight training sector as a sodium, magnesium or calcium salt.

However, 3-hydroxybutyric acid is not known or only in very small quantities to humans in evolutionary terms, since plants do not produce 3-hydroxybutyric acid and 3-hydroxybutyric acid in the animal organism only occurs in dead emaciated animals in ketosis, so that 3-hydroxybutyric acid causes nausea when administered orally. 3-Hydroxybutyric acid in the form of free acid and its salts also taste very bitter and can cause severe vomiting and nausea.

Moreover, patients, especially newborns, but also adults cannot permanently tolerate large amounts of salts of 3-hydroxybutyric acid, as these compounds can have a kidney-damaging effect.

In addition, the plasma half-life of 3-hydroxybutyric acid and its salts is so short that even if several grams are taken, the ketosis lasts only for about three to four hours, i.e. patients cannot benefit continuously from a therapy with 3-hydroxybutyric acid or its salts, especially at night. In case of metabolic diseases this can lead to life-threatening situations.

Therefore, in the case of the therapy of such metabolic diseases, so-called medium-chain triglycerides, so-called MCTs, are currently used for ketogenic therapy, i.e. the metabolic conversion of caproic, caprylic and capric acid (i.e. of saturated linear $C_6$-, $C_8$- and $C_{10}$-fatty acids) from the corresponding triglycerides is intended.

Basically, however, from a pharmaceutical and clinical point of view, 3-hydroxybutyric acid is a more effective pharmaceutical-pharmacological target molecule, which, according to the prior art, could in principle be used for the therapy of a large number of diseases, but cannot be used due to its lack of physiological compatibility (e. g. in diseases in connection with a malfunction of the energy metabolism, especially (keto-body metabolism, or neurodegenerative diseases such as dementia, Alzheimer's disease, Parkinson's disease, etc., lipometabolic diseases etc.).

The following table illustrates purely exemplary, but by no means limiting, potential therapy options or possible indications for the active ingredient 3-hydroxybutyric acid.

| Indication | Therapeutic effect |
| --- | --- |
| Traumatic brain injury | Under BHB the apoptosis and necrosis rate of nerve cells decreases. |
| Stroke | Under BHB the apoptosis and necrosis rate of nerve cells decreases. |
| Refeeding syndrome | In case of anorexia, discontinuation of enteral or parenteral nutrition and after long periods of hunger, the consumption of starch or glucose can lead to death (see also WHO scheme peanut paste). BHB can be used here as a therapeutic agent to achieve normal food intake more quickly. |
| Appetite suppressant | BHB suppresses the feeling of hunger in the central nervous system (CNS). |
| Epilepsy | Conventional ketogenic diet to significantly reduce the frequency of seizures has extremely poor patient tolerance. BHB offers an immediately effective alternative here. |
| Alzheimer's disease, dementia | Under BHB patients show better cognitive performance. BHB is also effective in the prevention of neurodegenerative diseases. |

-continued

| Indication | Therapeutic effect |
| --- | --- |
| Disorders of fatty acid oxidation (e.g. electron transfer protein defect) | Compensation of a nutrient deficiency in case of defect in energy metabolism. |

Therefore, it is desirable from a pharmaceutical and clinical point of view to be able to find effective precursors or metabolites which physiologically allow direct or indirect access to 3-hydroxybutyric acid or its salts, especially in the physiological metabolism of the human or animal body.

Consequently, the prior art has not lacked attempts to find physiologically suitable precursors or metabolites for 3-hydroxybutyric acid or its salts. So far, however, no efficient compounds have been found in the prior art. Also, access to such compounds is not or not readily possible according to the prior art.

BRIEF SUMMARY OF THE INVENTION

The problem underlying the present invention is thus the provision of an efficient method for producing physiologically suitable or physiologically compatible precursors and/or metabolites of 3-hydroxybutyric acid (i.e. beta-hydroxybutyric acid or BHB or 3-BHB) or their salts.

Such method should especially make the respective BHB precursors and/or BHB metabolites accessible in an efficient way, especially in larger quantities and without significant amounts of toxic by-products.

In a completely surprising way, the applicant has now discovered that polyol esters, especially polyglycerol esters, of optionally acylated 3-hydroxybutyric acid (beta-hydroxybutyric acid, BHB or 3-BHB) represent an efficient and physiologically effective or physiologically compatible precursor and/or metabolite for the keto body 3-hydroxybutyric acid or its salts and has in this context been able to find or develop an efficient method for producing these compounds, which allows direct and effective, especially economic as well as industrially feasible access to these compounds.

To solve the problem described above, the present invention therefore proposes—according to a first aspect of the present invention—a method for producing polyol esters, especially polyglycerol esters, of optionally acylated 3-hydroxybutyric acid (beta-hydroxybutyric acid, BHB or 3-BHB); further, especially special and/or advantageous embodiments of the inventive method are provided.

Furthermore, the present invention relates—according to a second aspect of the present invention—to a reaction product obtainable according to the inventive method provided or a polyol ester, especially polyglycerol ester, of optionally acylated 3-hydroxybutyric acid (beta-hydroxybutyric acid, BHB or 3-BHB) or a mixture of at least two, especially at least three polyol esters, especially polyglycerol esters, of optionally acylated 3-hydroxybutyric acid (beta-hydroxybutyric acid, BHB or 3-BHB) obtainable in this regard as provided herein; further, especially special and/or advantageous embodiments of this aspect of the invention are also disclosed.

Likewise, the present invention—according to a third aspect of the present invention—relates to a pharmaceutical composition, especially a drug or medicament; further, especially special and/or advantageous embodiments of this aspect of the invention are also provided.

Furthermore, the present invention—according to a fourth aspect of the present invention—relates to an inventive reaction product or an inventive polyol ester, especially polyglycerol ester, of optionally acylated 3-hydroxybutyric acid (beta-hydroxybutyric acid, BHB or 3-BHB) or an inventive mixture of at least two, especially at least three polyol esters, especially polyglycerol esters, of optionally acylated 3-hydroxybutyric acid (beta-hydroxybutyric acid, BHB or 3-BHB) for the prophylactic and/or therapeutic treatment or for use in the prophylactic and/or therapeutic treatment of diseases of the human or animal body.

Furthermore, the present invention—according to a fifth aspect of the present invention relates to the use of an inventive reaction product or an inventive polyol ester, especially polyglycerol ester, of optionally acylated 3-hydroxybutyric acid (beta-hydroxybutyric acid, BHB or 3-BHB) or of an inventive mixture of at least two, especially at least three polyol esters, especially polyglycerol esters, of optionally acylated 3-hydroxybutyric acid (beta-hydroxybutyric acid, BHB or 3-BHB) for the prophylactic and/or therapeutic treatment or for producing a medicament for the prophylactic and/or therapeutic treatment of diseases of the human or animal body.

Furthermore, the present invention—according to a sixth aspect of the present invention relates to the use of an inventive reaction product or an inventive polyol ester, especially polyglycerol ester, of optionally acylated 3-hydroxybutyric acid (beta-hydroxybutyric acid, BHB or 3-BHB) or an inventive mixture of at least two, especially at least three polyol esters, especially polyglycerol esters, of optionally acylated 3-hydroxybutyric acid (beta-hydroxybutyric acid, BHB or 3-BHB) for the prophylactic and/or therapeutic treatment or for producing a medicament for the prophylactic and/or therapeutic treatment of or for the application for catabolic metabolic states, such as hunger, diets or low-carbohydrate nutrition.

Furthermore, the present invention—according to a seventh aspect of the present invention—relates to a food and/or food product; further, especially special and/or advantageous embodiments of the food and/or food product according to the invention are also provided.

Finally, the present invention according to an eighth aspect of the present invention—relates to the use of an inventive reaction product or an inventive polyol ester, especially polyglycerol ester, of optionally acylated 3-hydroxybutyric acid (beta-hydroxybutyric acid, BHB or 3-BHB) or of an inventive mixture of at least two, especially at least three polyol esters, especially polyglycerol esters, of optionally acylated 3-hydroxybutyric acid (beta-hydroxybutyric acid, BHB or 3-BHB) in a food and/or a food product; further, especially special and/or advantageous embodiments of the use according to the invention are provided.

It goes without saying that following features, embodiments, advantages and the like, which are subsequently listed below only with regard to one aspect of the invention for the purpose of avoiding repetition, naturally also apply accordingly to the other aspects of the invention, without this requiring a separate mention.

Furthermore, it goes without saying that individual aspects and embodiments of the present invention are also considered disclosed in any combination with other aspects and embodiments of the present invention and, especially, any combination of features and embodiments, as it results from back references of all patent claims, is also considered extensively disclosed with regard to all resulting combination possibilities.

With respect to all relative or percentage weight-based data provided below, especially relative quantity or weight data, it should further be noted that within the scope of the present invention these are to be selected by the person skilled in the art such that they always add up to 100% or 100% by weight, respectively, including all components or ingredients, especially as defined below; however, this is self-evident for the person skilled in the art.

In addition, the skilled person may, if necessary, deviate from the following range specifications without leaving the scope of the present invention.

Additionally, it applies that all values or parameters or the like specified in the following can be determined or identified in principle with standardized or explicitly specified determination methods or otherwise with the determination or measurement methods that are otherwise familiar to a person skilled in the art.

Having stated this, the present invention will be described in more detail hereinafter:

DETAILED DESCRIPTION OF THE INVENTION

The subject-matter of the present invention—according to a first aspect of the present invention—is thus a method for producing polyol esters, especially polyglycerol esters, of optionally acylated 3-hydroxybutyric acid (beta-hydroxybutyric acid, BHB and/or 3-BHB), wherein at least one compound of the general formula (I)

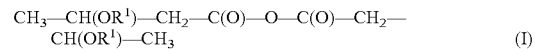

wherein, in the general formula (I), the radical $R^1$ represents an acyl group selected from —C(O)—CH$_3$ (acetyl group) or —C(O)—C$_2$H$_5$ (propionyl group), preferably —C(O)—CH$_3$ (acetyl group), is reacted with at least one polyol (II) comprising at least two hydroxyl groups (OH-groups), especially polyglycerol, optionally followed by hydrolysis of the acyl groups, so that, as a reaction product (III), one or more polyol esters, especially polyglycerol esters, of optionally acylated 3-hydroxybutyric acid are obtained.

As stated hereinabove, the applicant has, quite surprisingly, discovered that the polyol esters, especially polyglycerol esters, of optionally acylated 3-hydroxybutyric acid (beta-hydroxybutyric acid, BHB or 3-BHB) thus produced are efficient, since physiologically compatible precursors and/or metabolites of 3-hydroxybutyric acid or their salts, which can also be used in larger quantities in pharmaceutical or clinical applications because they are physiologically compatible.

The above-mentioned polyol esters, especially polyglycerol esters, of optionally acylated 3-hydroxybutyric acid, which are accessible for the first time in an efficient manner through the production method according to the invention, represent a physiologically and pharmacologically relevant alternative to free 3-hydroxybutyric acid or its salts.

The production of polyol esters, especially polyglycerol esters, of optionally acylated 3-hydroxybutyric acid by means of conventional organic synthesis is complex and costly, since 3-hydroxybutyric acid has an increased tendency to polymerize and to undergo other undesirable side reactions (e. g. dehydration, decomposition, etc.). Within the scope of the present invention, it was possible for the first time to provide an efficiently working production method with which polyol esters, especially polyglycerol esters, of optionally acylated 3-hydroxybutyric acid can be produced without undesired side reactions, especially in a single step.

The inventive method thus makes it possible for the first time to provide non-toxic polyol esters, especially polyglycerol esters, of optionally acylated 3-hydroxybutyric acid from known, commercially available and above all physiologically harmless components or educts (starting compounds). The resulting polyol esters, especially polyglycerol esters, of optionally acylated 3-hydroxybutyric acid can be broken down physiologically, especially in the stomach and/or bowl, and release or generate the target molecule "3-hydroxybutyric acid" or its salts as active ingredient or active component.

In addition, the aforementioned polyol esters, especially polyglycerol esters, of optionally acylated 3-hydroxybutyric acid also comprise an acceptable taste to ensure compatibility even when administered orally in larger quantities over a longer period of time (e.g. administration of 50 g daily dose or more).

Similarly, the production method according to the invention makes it possible to provide the polyol esters, especially polyglycerol esters, of optionally acylated 3-hydroxybutyric acid free from toxic impurities.

In addition, with appropriate starting materials, the method can also be carried out enantioselectively. For example, according to the invention, the production method allows the biologically relevant form, i.e. the (R)-enantiomer, to be enriched so as not to burden the renal system of patients when administered orally (i.e. elimination via the kidneys). In principle, however, it is also possible, and under certain conditions may be useful, to enrich the (S)-enantiomer.

In addition, the production method according to the invention, including optional further processing or purification steps, can be operated economically and can also be implemented on a large scale.

Especially, the inventive production method uses commercially available starting compounds and furthermore allows a relatively simple process management even in case of large-scale implementation.

In contrast to conventional prior art production methods, the production method according to the invention does not use complex starting materials and uses only a single step. Nevertheless, excellent yields are achieved in accordance with the invention, wherein the formation of by-products is minimized or avoided.

In addition, the inventive method is simple and economical. Especially, the method according to the invention is usually carried out in the absence of solvents and/or without any solvent (i.e. as a reaction in mass or as a reaction in substance or as a so-called bulk reaction); consequently, the reaction products obtained are not contaminated with solvent and no solvent has to be removed and disposed of or recycled in a costly and energy-intensive manner after the method or reaction has been carried out. Furthermore, no toxic by-products are formed.

The production method according to the invention usually results in a mixture of different polyol esters, especially polyglycerol esters, of optionally acylated 3-hydroxybutyric acid, i.e. in a mixture of at least two, especially at least three different polyol esters, especially polyglycerol esters, of optionally acylated 3-hydroxybutyric acid. The resulting raw reaction product or raw mixture can be purified by known methods, especially by removing any remaining starting compounds and/or any by-products present, and furthermore—if desired—can be separated by known methods, especially by distillation and/or chromatography (e.g. fractionation into the individual polyol esters, i.e. mono-, di-, tri- etc. polyol esters of optionally acylated 3-hydroxybutyric acid, or else fractionation into fractions with enriched and depleted portions of individual polyol esters etc.).

According to a particular embodiment of the present invention, the compound of the general formula (I) may be used in racemic form or in the form of the (R)-enantiomer. The (R)-configuration refers to the two chiral carbon atoms of the compound of the general formula (I), i.e. the carbon atoms marked "*" below in the compound of the general formula (I), each of these chiral centers corresponding to the C-atom in the 3-position of 3-hydroxybutyric acid:

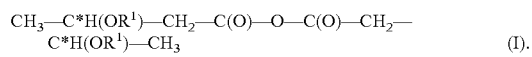

$$CH_3—C^*H(OR^1)—CH_2—C(O)—O—C(O)—CH_2—C^*H(OR^1)—CH_3 \qquad (I).$$

According to the invention, it is preferred if, in the general formula (I), the radical $R^1$ represents a group $C(O)—CH_3$ (acetyl group).

In other words, it is preferred according to the invention that, as a compound of the general formula (I), the compound of the formula $CH_3—CH(OAc)—CH_2—C(O)—O—C(O)—CH_2—CH(OAc)—CH_3$, wherein Ac represents an acetyl group, is used.

This enables particularly efficient process control and high yields with minimized or suppressed by-product formation. In addition, the starting compound of the general formula (I) can be readily prepared from conventional, commercially available reactants and is also economically more efficient to convert than the free acid (i.e. 3-hydroxybutyric acid).

Especially, in the inventive method, the reaction is carried out in the absence of solvents and/or without any solvent. I.e., the reaction is thus carried out as a reaction in mass or as a reaction in substance or as a so-called bulk reaction. This has the advantage that the reaction products obtained are not contaminated with solvent and that no solvent has to be removed and disposed of or recycled in a costly and energy-intensive manner after the method or reaction has been carried out. Surprisingly, the method or reaction nevertheless proceeds with high conversion and yields and at least essentially without significant by-product formation.

According to a particular embodiment of the present invention, the reaction may be carried out autocatalytically or in the presence of a catalyst, especially a mineral acid, preferentially autocatalytically. in this particular embodiment, it is preferred that the reaction is carried out autocatalytically (i.e. in the absence of an additional catalyst).

Within the scope of the inventive method, the temperatures during the reaction can vary within wide ranges. Especially, the reaction can be carried out at temperatures in the range of from 20° C. to 150° C., especially in the range of from 50° C. to 140° C., preferentially in the range of from 60° C. to 130° C., more preferably in the range of from 70° C. to 125° C., even more preferably in the range of from 75° C. to 110° C. Nevertheless, it may be necessary, depending on the application or individual case, to deviate from the above-mentioned values without leaving the scope of the present invention.

Within the scope of the inventive method, the pressures during the reaction can also vary within wide ranges, Especially, the reaction can be carried out at a pressure in the range of from 0.0001 bar to 10 bar, especially in the range of from 0.001 bar to 5 bar, preferentially in the range of from 0.01 bar to 2 bar, more preferably in the range of from 0.05 bar to 1 bar, even more preferably at about 1 bar. Nevertheless, it may be necessary, depending on the application or individual case, to deviate from the above-mentioned values without leaving the scope of the present invention.

As far as the quantity of starting materials or starting compounds is concerned, this can also be varied within a wide range.

Taking into account process economy and optimization of the course of the method, especially with regard to the minimization of by-products, it is advantageous if the compound of the general formula (I), based on the hydroxyl groups of the polyol (II), especially polyglycerol, is used in molar amounts in a range of from equimolar amount up to a molar excess of 200 mol-%, especially in a range of from equimolar amount up to a molar excess of 150 mol-%, preferentially in a range of from equimolar amount up to a molar excess of 100 mol-%.

Similarly, taking into account process economy and optimization of the course of the method, especially with regard to minimizing by-products, it is advantageous if the compound of the general formula (I) and the polyol (II), especially polyglycerol, are used in a molar ratio of compound of the general formula (I)/polyol (II) in a range of from 1:1 to 10:1, especially in a range of from 2:1 to 8:1, preferentially in a range of from 3:1 to 6:1.

As far as the polyol (II) usable in the method according to the invention is concerned, it is particularly preferred if the polyol (II) comprises at least three hydroxyl groups (OH-groups).

According to a special embodiment of the inventive method, it may especially be provided that the polyol (II) corresponds to the general formula (IIa)

  (IIa)

wherein, in the general formula (IIa),
X represents an organic radical, especially a preferentially saturated organic radical comprising 4 to 20 carbon atoms and optionally comprising 1 to 9 oxygen atoms, preferentially selected from an alkyl radical or a (poly)alkyl ether radical, especially (poly)alkylene glycol radical, more preferably selected from a $C_4$-$C_{20}$-alkyl radical or a $C_4$-$C_{20}$-(poly)alkyl ether radical, especially a $C_4$-$C_{20}$-(poly)alkylene glycol radical; and
the variables m and n, each independently of one another, represent an integer from 1 to 10.

Especially, according to the invention, it is preferred in this context that the hydroxyl groups of the polyol (II) are in any position of the radical X, preferentially wherein at least one hydroxyl group is terminal (i.e. being a primary hydroxyl group). This means in particular that the hydroxyl groups can be located or provided in any position of the organic radical X (preferably, however, with the proviso that at least one hydroxyl group is terminal and/or is a primary hydroxyl group).

Especially, the polyol (II), which can be used within the scope of the inventive method, may be selected from polyether polyols and alkane polyols and combinations thereof, especially $C_4$-$C_{20}$-polyether polyols and $C_4$-$C_{20}$-alkane polyols, preferentially $C_4$-$C_{20}$-polyether polyols and $C_4$-$C_{20}$-alkane diols, more preferably polyether polyols, even more preferably $C_4$-$C_{20}$-polyether polyols.

According to a particular embodiment of the method according to the invention, the polyol (II) may be selected from polyether polyols, especially $C_4$-$C_{20}$-polyether polyols, preferentially polyglycerols of the general formula (IIb)

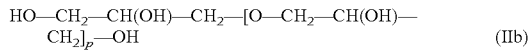  (IIb)

wherein, in the general formula (IIb), the variable p represents an integer from 1 to 4, especially 1 or 2, preferentially 1.

According to another special embodiment of the method according to the invention, the polyol (II) may be a diglycerol of formula (IIc)

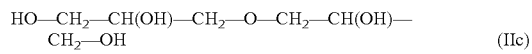  (IIc)

According to yet a further special embodiment of the method according to the invention, the polyol (II) may be selected from alkanediols, especially $C_1$-$C_{20}$-alkanediols, preferentially linear or branched alkanediols, preferably linear or branched $C_1$-$C_{20}$-alkanediols, more preferably linear $C_4$-$C_{20}$-alkanediols, even more preferably linear $C_4$-$C_{20}$-alkanediols having at least one terminal and/or primary hydroxyl group, yet even more preferably pentanediol, especially 1,2-pentanediol.

According to a preferred embodiment of the present invention, the present invention according to this aspect of the invention relates to a method for producing polyol esters, especially polyglycerol esters, of optionally acylated 3-hydroxybutyric acid (beta-hydroxybutyric acid, BHB and/or 3-BHB), especially a method as defined hereinabove,
wherein at least one compound of the general formula (I)

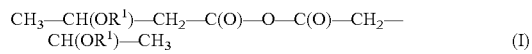  (I)

wherein, in the general formula (I), the radical $R^1$ represents an acyl group selected from —C(O)—CH$_3$ (acetyl group) or —C(O)—C$_2$H$_5$ (propionyl group), preferably —C(O)—CH$_3$ (acetyl group),
is reacted with at least one polyol (II) comprising at least two hydroxyl groups (OH-groups), especially polyglycerol, wherein the polyol (II) is selected from polyether polyols, especially $C_4$-$C_{20}$-polyether polyols, preferentially polyglycerols of the general formula (IIb)

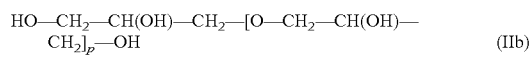  (IIb)

wherein, in general formula (IIb), the variable p represents an integer from 1 to 4, especially 1 or 2, preferentially 1,
optionally followed by hydrolysis of the acyl groups,
so that, as a reaction product (III), one or more polyol esters, especially polyglycerol esters, of optionally acylated 3-hydroxybutyric acid are obtained.

According to a further preferred embodiment of the present invention, the present invention relates, according to this aspect of the invention, to a method for producing polyol esters, especially polyglycerol esters, of optionally acylated 3-hydroxyburic acid (beta-hydroxybutyric acid, BHB and/or 3-BHB), especially a method as defined hereinabove,
wherein at least one compound of the general formula (I)

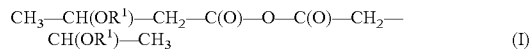  (I)

wherein, in the general formula (I), the radical $R^1$ represents a group —C(O)—CH$_3$ (acetyl group),
is reacted with at least one polyol (II) comprising at least two hydroxyl groups (OH-groups), especially polyglycerol, wherein the polyol (II) is selected from polyglycerols of the general formula (IIb)

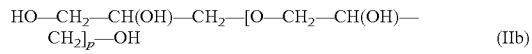  (IIb)

wherein, in the general formula (IIb), the variable p represents an integer 1 or 2, preferably 1, optionally followed by hydrolysis of the acetyl groups, so that, as a reaction product (III), one or more polyol esters, especially polyglycerol esters, of optionally acylated 3-hydroxybutyric acid are obtained.

In the method according to the invention, during the reaction, the compound according to the general formula (IV)

$$R^1\text{—OH} \qquad \text{(IV)}$$

is formed simultaneously, wherein, in the general formula (IV), the radical $R^1$ has the meaning defined hereinabove.

Especially it is preferred in this context if the compound according to the general formula (IV) is withdrawn from the reaction after the reaction has been performed, especially by means of removal by distillation.

In the production method according to the invention, the reaction product (III), especially the composition of the reaction product (III), especially the presence of the various polyol esters, especially polyglycerol esters, of optionally acylated 3-hydroxybutyric acid and their proportion in the case of a mixture, may be controlled and/or regulated by means of the reaction conditions, especially by selecting the reaction temperature (conversion temperature) and/or by selecting the reaction pressure (conversion pressure) and/or by providing a catalyst and selecting such catalyst with respect to the type and/or amount and/or by selecting the amounts of starting compounds (educts).

After the reaction, the reaction product obtained can be subjected to further purification or work-up steps.

In this context, the reaction product obtained can be fractionated after the reaction has been performed, especially fractionated by distillation.

Also, unreacted starting compounds (I) and/or (II) can be separated from the reaction product and are subsequently recycled.

As already explained above in connection with the inventive method, within the scope of the method of the invention—according to a particular embodiment—the reaction of the at least one compound of the general formula (I) with the at least one polyol (II), especially polyglycerol, as described hereinabove, can optionally be followed by hydrolysis of the acyl groups. This embodiment of the inventive method is preferred if the reaction product (III) is to be free from acyl groups. For this purpose, according to the invention, a selective or partial hydrolysis of the acyl groups present in the reaction products obtained after reaction is performed (which are located in the 3-position of the 3-hydroxybutyric acid part of the reaction products obtained after reaction). Thus, reaction products (III), as defined below (i.e. subsequent general formulae (IIIa), (IIIb) and (IIIc)) can be obtained, wherein $R^1$ represents a hydrogen atom (i.e. replacement of the acyl group by a hydrogen atom in the course of hydrolysis).

Especially, it is preferred if, according to this embodiment of the inventive method, the hydrolysis of the acyl groups, especially of the acetyl groups, takes place in the presence of a catalyst, preferentially an enzyme. This ensures selective or partial hydrolysis of the acyl groups, especially under mild and economical conditions, preferentially avoiding the formation of by-products.

Especially, the enzyme used for the hydrolysis of the acyl groups, especially the acetyl groups, may be selected from synthetases (ligases), catalases, esterases, lipases and combinations thereof. According to the invention, synthetases (synonymously ligases) are especially enzymes from the class of ligases; ligases are enzymes which catalyze the linking of two or more molecules by a covalent bond. Catalases in the sense of the present invention are especially enzymes which are capable of converting hydrogen peroxide to oxygen and water. The term esterases refers in particular to enzymes which are capable of hydrolytically splitting esters into alcohol and acid (saponification); these are thus especially hydrolases, wherein fat splitting esterases are also called lipases. Lipases in the sense of the present invention are especially enzymes which are capable of splitting free fatty acids from lipids such as glycerides (lipolysis).

Especially, the enzyme used for the hydrolysis of the acyl groups, especially the acetyl groups, may be derived from *Candida antarctica, Mucor miehei (Rhizomucor miehei), Thermomyces lanuginosus, Candida rugosa, Aspergillus oryzae, Pseudomonas cepacia, Pseudomonas fluorescens, Rhizopus delemar* and *Pseudomonas* sp. and combinations thereof, preferentially of *Candida antarctica, Mucor miehei (Rhizomucor miehei)* and *Thermomyces lanuginosus*.

Especially, the enzyme used for the hydrolysis of the acyl groups, especially the acetyl groups, can be used in immobilized form, especially immobilized on a carrier, preferentially on a polymeric carrier, preferably on a polymeric organic carrier, more preferably with hydrophobic properties, even more preferably on a poly(meth)acrylic resin-based carrier.

Especially, the enzyme used for the hydrolysis of the acyl groups, especially the acetyl groups, can be used in amounts, based on the total amount of the compound to be hydrolyzed, in the range of from 0.001% by weight to 20% by weight, especially in the range of from 0.01. % by weight to 15% by weight, preferentially in the range of from 0.1% by weight to 15% by weight, preferably in the range of from 0.5% by weight to 10% by weight.

In this particular embodiment, it is preferred that the enzyme used for the hydrolysis of the acyl groups, especially the acetyl groups, is recycled after the hydrolysis.

The optionally carried out hydrolysis of the acyl groups, especially of the acetyl groups, can be carried out especially at temperatures in the range of from 10° C. to 80° C., especially in the range of from 20° C. to 80° C., preferentially in the range of from 25° C. to 75° C., more preferably in the range of from 45° C. to 75° C., even more preferably in the range of from 50° C. to 70° C.

The optionally carried out hydrolysis of the acyl groups, especially of the acetyl groups, can be carried out especially at a pressure in the range of from 0.0001 bar to 10 bar, especially in the range of from 0.001 bar to 5 bar, preferentially in the range of from 0.01 bar to 2 bar, more preferably in the range of from 0.05 bar to 1 bar, even more preferably at about 1 bar.

Typically, the hydrolysis of the acyl groups, especially the acetyl groups, is carried out in the presence of water.

According to this particular embodiment of the inventive method, according to which the previously described reaction of the at least one compound of the general formula (I) with the at least one polyol (II), especially polyglycerol, is followed by hydrolysis of the acyl groups, commercially available enzymes of the aforementioned definition can be used as the previously described enzyme e.g. CALB lipase on polymer support, derived from *Candida antarctica*, e.g. Novozym® 435 from Sigma-Aldrich or Merck or Lipozym® 435 from Merck).

According to a particular embodiment of the production method according to the invention, it is possible to proceed especially such that hydroxyl groups still present in the reaction product after the reaction is performed are at least partially, preferentially completely, functionalized, especially esterified. Especially, the reaction can be followed by a partial, especially complete, functionalization, especially esterification, of hydroxyl groups still available.

In this particular embodiment of the inventive method, especially the functionalization, especially esterification, of the hydroxyl groups can be carried out by reaction with a carboxylic acid anhydride, especially $C_2$-$C_{30}$-carboxylic acid anhydride, preferably $C_2$-$C_{10}$-carboxylic acid anhydride, preferentially $C_7$-carboxylic acid anhydride. The $C_2$-$C_{30}$-carboxylic acid anhydride, preferably $C_2$-$C_{10}$-carboxylic acid anhydride, preferentially $C_7$-carboxylic acid anhydride, can be a linear (straight-chained) or branched, saturated or mono- or polyunsaturated $C_2$-$C_{30}$-carboxylic acid anhydride, preferably $C_2$-$C_{10}$-carboxylic acid anhydride, preferentially $C_7$-carboxylic acid anhydride.

In a further particular embodiment of the inventive method, especially the functionalization, especially esterification, of the hydroxyl groups can be carried out by reaction with a carboxylic acid anhydride, especially with a compound of the general formula (I) as defined hereinabove.

A particularly preferred approach according to the invention, which includes a functionalization, especially esterification, of hydroxyl groups still present following the reaction, including hydrolysis of the acyl groups, is illustrated by the following reaction or synthesis scheme with diglycerol as starting polyol (wherein, depending on the reaction procedure during the reaction, either individual esters or a mixture of two or more thereof are obtained and wherein, in the following reaction or synthesis scheme, the radical Y represents either a radical of the formula $CH_3$—$(CH_2)_{x=0-28}$—$C(O)$—, if the functionalization is carried out with a $C_2$-$C_{30}$-carboxylic acid anhydride, or a radical of the formula $CH_3$—$CH(OR^1)$—$CH_2$—$C(O)$—, wherein the radical $R^1$ has the meaning defined hereinabove, if the functionalization is carried out with a carboxylic acid anhydride corresponding to a compound of the general formula (I) as defined hereinabove):

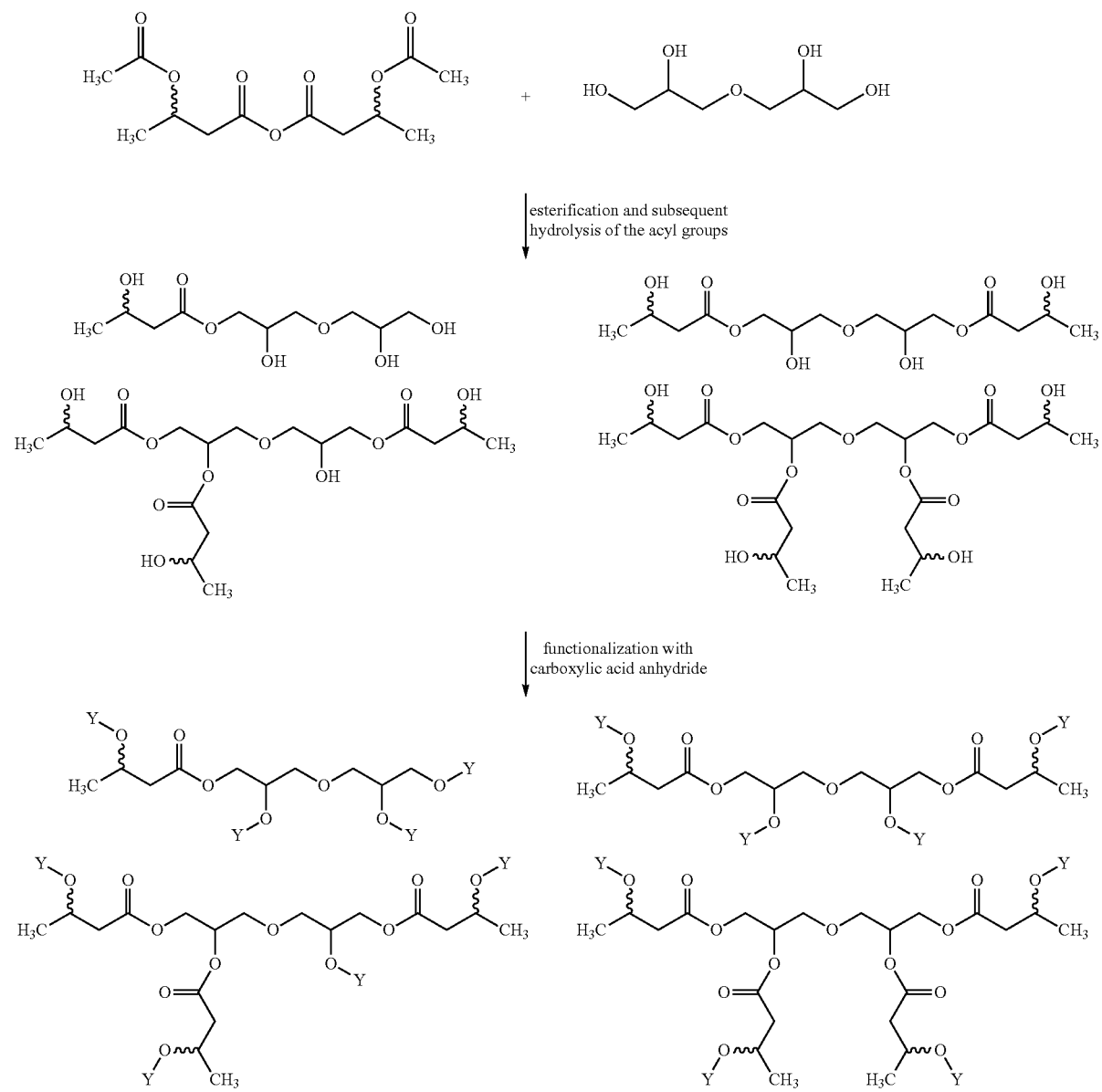

As far as the compound of general formula (I), as defined hereinabove, used in the inventive method is concerned, it is obtainable and/or obtained by reacting a carboxylic acid anhydride of formula (V)

wherein the radical $R^1$ has the meaning defined hereinabove, especially acetic anhydride or propionic anhydride, preferentially acetic anhydride, with 3-hydroxybutyric acid.

Especially, the reaction of carboxylic acid anhydride of formula (V) with 3-hydroxybutyric acid may take place according to the reaction equation

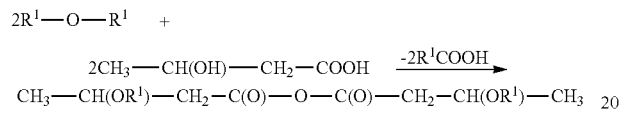

wherein the radical $R^1$ has the meaning defined hereinabove.

According to a particular embodiment, the reaction of acetic anhydride with 3-hydroxybutyric acid may take place according to the reaction equation

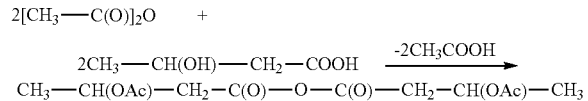

wherein the radical Ac represents an acetyl group.

The temperatures of the reaction of carboxylic acid anhydride of formula (V), as defined hereinabove, with 3-hydroxybutyric acid can vary within wide ranges. Especially, the reaction of carboxylic acid anhydride of formula (V), as defined hereinabove, with 3-hydroxybutyric acid can be carried out at temperatures in the range of from 60 to 150° C., especially in the range of from 70 to 120° C., preferentially in the range of from 80 to 100° C.

The pressures of the reaction of carboxylic acid anhydride of formula (V), as defined hereinabove, with 3-hydroxybutyric acid can equally vary within wide ranges. Especially, the reaction of carboxylic acid anhydride of formula (V), as defined hereinabove, with 3-hydroxybutyric acid can be carried out at a pressure in the range of from 0.0001 bar to 10 bar, especially in the range of from 0.001 bar to 5 bar, preferentially in the range of from 0.01 bar to 2 bar, more preferably in the range from 0.05 bar to 1 bar, even more preferably at about 1 bar.

According to a particular embodiment of the inventive method, the present invention relates to a method for producing polyol esters, especially polyglycerol esters, of optionally acylated 3-hydroxybutyric acid (beta-hydroxybutyric acid, BHB and/or 3-BHB), especially a method as defined hereinabove, wherein
(a) in a first process step (a) a carboxylic acid anhydride of the previously defined formula (V)

wherein the radical $R^1$ has the meaning defined hereinabove, especially acetic anhydride or propionic anhydride, preferentially acetic anhydride, is reacted with 3-hydroxybutyric acid to obtain a compound of the general formula (I) as defined hereinabove; and subsequently
(b) in a second process step (b), the compound of general formula (I), as defined hereinabove, thus obtained is reacted with at least one polyol (II) comprising at least two hydroxyl groups (OH-groups), especially polyglycerol, as defined hereinabove;
(c) optionally followed by a third process step (c) of hydrolysis of the acyl groups, so that, as a reaction product (III), one or more polyol esters, especially polyglycerol esters, of optionally acylated 3-hydroxybutyric acid are obtained.

Within the scope of the inventive method, it is possible to obtain, as a reaction product (III), one or more polyol esters, especially polyglycerol esters, of optionally acylated 3-hydroxybutyric acid of the general formula (IIIa)

$$(R^2O)_m-(X)-(OR^2)_n \qquad (IIIa)$$

wherein, in the general formula (IIIa),
X represents an organic radical, especially a preferentially saturated organic radical comprising 4 to 20 carbon atoms and optionally comprising 1 to 9 oxygen atoms, preferentially selected from an alkyl radical or a (poly)alkyl ether radical, especially a (poly)alkylene glycol radical, more preferably selected from a $C_4$-$C_{20}$-alkyl radical or a $C_4$-$C_{20}$-(poly)alkyl ether radical, especially a $C_4$-$C_{20}$-(poly) alkylene glycol radical,
the variables m and n, each independently of one another, represent an integer from 1 to 10,
$R^2$, independently of one another, represents: hydrogen, a radical $CH_3$—$CH(OH)$—$CH$—$C(O)$— or a radical $CH_3$—$CH(OR^1)$—$CH_2$—$C(O)$— with $R^1$=acyl group selected from —$C(O)$—$CH_3$ (acetyl group) or —$C(O)$—$C_2H_5$ (propionyl group), preferably —$C(O)$—$CH_3$ (acetyl group), however, with the proviso that at least one radical $R^2$, especially at least two radicals $R^2$, does not represent hydrogen, and/or with the proviso that at least one radical $R^2$, especially at least two radicals $R^2$, represents a radical $CH_3$—$CH(OH)$—$CH_2$—$C(O)$— or a radical $CH_3$—$CH(OR^1)$—$CH_2$—$C(O)$— with $R^1$ as defined hereinabove.

Especially the groups $R^2O$— can be in any position of the radical X (preferably wherein at least one group $R^2O$— is terminal).

Especially, according to a particular embodiment, in the general formula (IIIa), $R^2$, independently of one another, may represent hydrogen or a radical $CH_3$—$CH(OH)$—$CH_2$—$C(O)$—, however, with the proviso that at least one radical $R^2$, especially at least two radicals $R^2$, does not represent hydrogen and/or with the proviso that at least one radical $R^2$, especially at least two radicals $R^2$, represents a radical $CH_3$—$CH(OH)$—$CH_2$—$C(O)$—.

Furthermore, according to another particular embodiment, in the general formula (IIIa), $R^2$, independently of one another, may represent hydrogen or a radical $CH_3$—$CH(OR^1)$—$CH_2$—$C(O)$— with $R^1$ as defined hereinabove, however, with the proviso that at least one radical $R^2$, especially at least two radicals $R^2$, does not represent hydrogen and/or with the proviso that at least one radical $R^2$, especially at least two radicals $R^2$, represents a radical $CH_3$—$CH(OR^1)$—$CH_2$—$C(O)$— with $R^1$ as defined hereinabove.

Furthermore, according to yet another particular embodiment, in the general formula (IIIa), $R^2$, independently of one another, may represent: a radical CH$_3$—CH(OH)—CH$_2$—C(O)— or a radical CH$_3$—CH(OR$^1$)—CH$_2$—C(O)— with R$^1$ as defined hereinabove.

Especially, in the production method according to the invention, as a reaction product (III), one or more polyol esters, especially polyglycerol esters, of optionally acylated 3-hydroxybutyric acid of the general formula (IIIb)

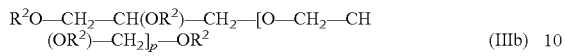 (IIIb)

may be obtained,
wherein, in the general formula (IIIb),
the variable p represents an integer from 1 to 4, especially 1 or 2, preferentially 1,
R$^2$, independently of one another, represents: hydrogen, a radical CH$_3$—CH(OH)—CH$_2$—C(O)— or a radical CH$_3$—CH(OR$^1$)—CH$_2$—C(O)— with R$^1$ acyl group selected from —C(O)—CH$_3$ (acetyl group) or —C(O)—C$_2$H$_5$ (propionyl group), preferably —C(O)—CH$_3$ (acetyl group), however, with the proviso that at least one radical R$^2$, especially at least two radicals R$^2$, does not represent hydrogen, and/or with the proviso that at least one radical R$^2$, especially at least two radicals R$^2$, represents a radical CH$_3$—CH(OH)—CH$_2$—C(O)— or a radical CH$_3$—CH(OR$^1$)—CH$_2$—C(O)— with R$^1$ as defined hereinabove.

Especially, according to a particular embodiment, in the general formula (IIIb), R$^2$, independently of one another, may represent hydrogen or a radical CH$_3$—CH(OH)—CH$_2$—C(O)—, however, with the proviso that at least one radical R$^2$, especially at least two radicals R$^2$, does not represent hydrogen and/or with the proviso that at least one radical R$^2$, especially at least two radicals R$^2$, represents a radical CH$_3$—CH(OH)—CH$_2$—C(O)—.

Furthermore, according to another particular embodiment, in the general formula (IIIb), R$^2$, independently of one another, may represent hydrogen or a radical CH$_3$—CH(OR$^1$)—CH$_2$—C(O)— with R$^1$ as defined hereinabove, however, with the proviso that at least one radical R$^2$, especially at least two radicals R$^2$, does not represent hydrogen and/or with the proviso that at least one radical R$^2$, especially at least two radicals R$^2$, represents a radical CH$_3$—CH(OR$^1$)—CH$_2$—C(O)— with R$^1$ as defined hereinabove.

Furthermore, according to yet another particular embodiment, in the general formula (IIIb), R$^2$, independently of one another, may represent: a radical CH$_3$—CH(OH)—CH$_2$—C(O)— or a radical CH$_3$—CH(OR$^1$)—CH$_2$—C(O)— with R$^1$ as defined hereinabove.

According to a particular embodiment of the method according to the invention, as a reaction product (III), one or more polyol esters, especially polyglycerot esters, of optionally acylated 3-hydroxybutyric acid of the general formula (IIIc)

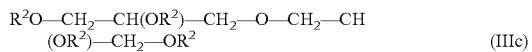 (IIIc)

may be obtained,
wherein, in the general formula (IIIc), R$^2$, independently of one another, represents: hydrogen, a radical CH$_3$—CH(OH)—CH$_2$—C(O)— or a radical CH$_3$—CH(OR$^1$)—CH$_2$—C(O)— with R$^1$=acyl group selected from —C(O)—CH$_3$ (acetyl group) or —C(O)—C$_2$H$_5$ (propionyl group), preferably —C(O)—CH$_3$ (acetyl group), however, with the proviso that at least one radical R$^2$, especially at least two radicals R$^2$, does not represent hydrogen, and/or with the proviso that at least one radical R$^2$, especially at least two radicals R$^2$, represents a radical CH$_3$—CH(OH)—CH$_2$—C(O)— or a radical CH$_3$—CH(OR$^1$)—CH$_2$—C(O)— with R$^1$ as defined hereinabove.

Especially, according to a particular embodiment, in the general formula (IIIc), R$^2$, independently of one another, may represent hydrogen or a radical CH$_3$—CH(OH)—CH$_2$—C(O)—, however, with the proviso that at least one radical R$^2$, especially at least two radicals R$^2$, does not represent hydrogen and/or with the proviso that at least one radical R$^2$, especially at least two radicals R$^2$, represents a radical CH$_3$—CH(OH)—CH$_2$—C(O)—.

Furthermore, according to another particular embodiment, in the general formula (IIIc), R$^2$, independently of one another, may represent hydrogen or a radical CH$_3$—CH(OR$^1$)—CH$_2$—C(O)— with R$^1$ as defined hereinabove, however, with the proviso that at least one radical R$^2$, especially at least two radicals R$^2$, does not represent hydrogen and/or with the proviso that at least one radical R$^2$, especially at least two radicals R$^2$, represents a radical CH$_3$—CH(OR$^1$)—CH$_2$—C(O)— with R$^1$ as defined hereinabove.

Furthermore, according to yet another particular embodiment, in the general formula (IIIc), R$^2$, independently of one another, may represent: a radical CH$_3$—CH(OH)—CH$_2$—C(O)— or a radical CH$_3$—CH(OR$^1$)—CH$_2$—C(O)— with R$^1$ as defined hereinabove.

According to a further particular embodiment of the method according to the invention, as a reaction product (Ill), a mixture of at least two different polyol esters, especially polyglycerol esters, of optionally acylated 3-hydroxybutyric acid, especially as defined hereinabove, may be obtained.

According to a further particular embodiment of the method according to the invention, as a reaction product (III), a mixture of at least three different polyol esters, especially polyglycerol esters, of optionally acylated 3-hydroxybutyric acid, especially as defined hereinabove, may be obtained.

As mentioned hereinbefore, the method according to the invention is usually carried out in the absence of solvents and/or without any solvent (i.e. as a reaction in mass or as a reaction in substance or as a so-called bulk reaction). This has the advantage that the reaction products obtained are not contaminated with solvent and no solvent has to be removed and disposed of or recycled in a costly and energy-intensive manner after the method or reaction has been carried out. Surprisingly, the method or reaction nevertheless proceeds with high conversions and yields and at least essentially without significant by-product formation.

A particularly preferred approach according to the invention is illustrated by the following reaction or synthesis scheme (wherein, depending on the reaction procedure, either individual esters or a mixture of two or more thereof are obtained):

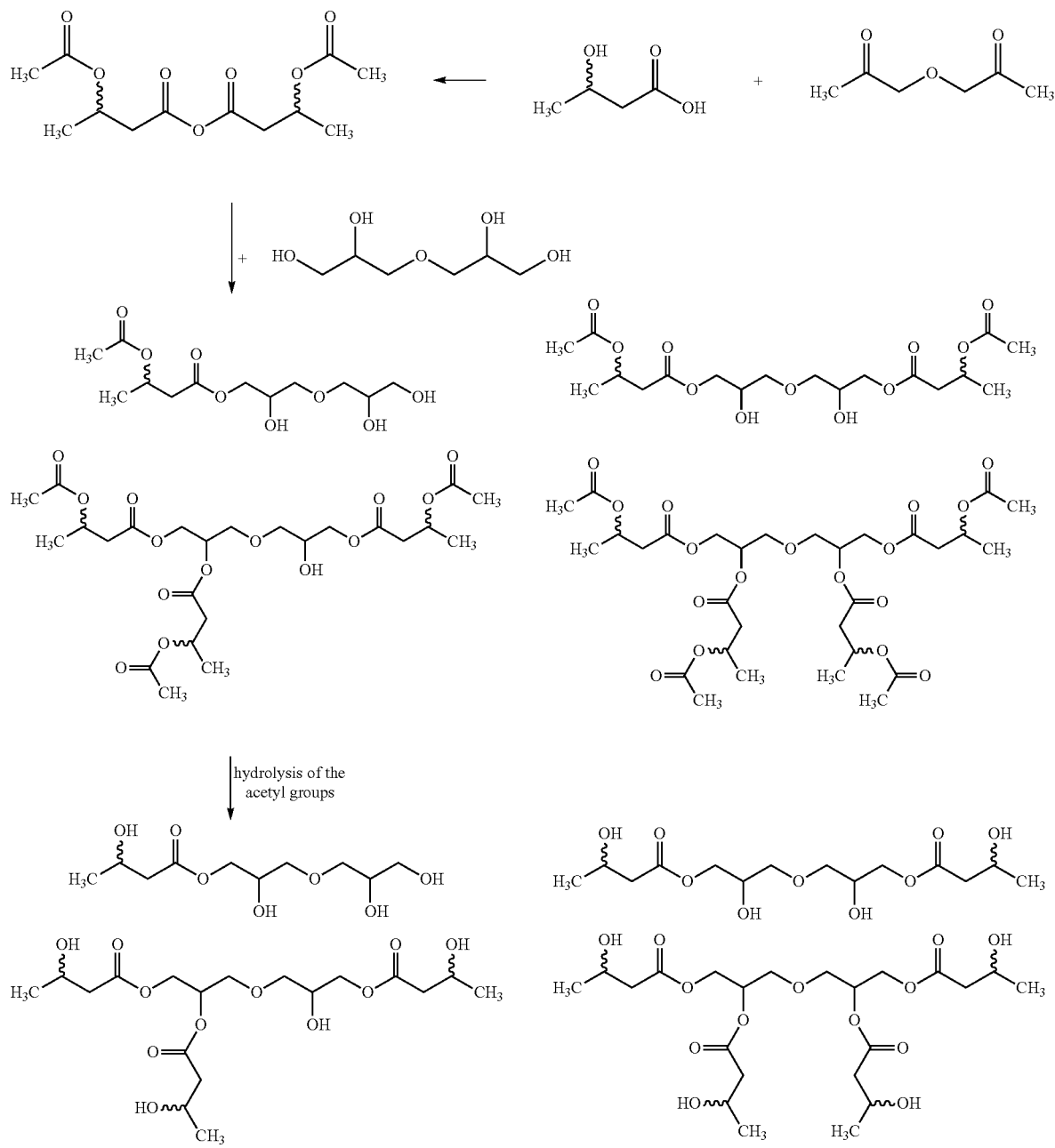

As explained hereinabove, the above reaction or synthesis scheme can optionally be followed by a functional nation of any remaining or still free OH-groups, as described hereinabove.

A further subject-matter—according to a second aspect of the present invention—is the reaction product obtainable according to the inventive method or the inventive reaction product as defined hereinabove, respectively, (i.e. one or more polyol esters, especially polyglycerol esters, of optionally acylated 3-hydroxybutyric acid or mixtures thereof).

Especially, the reaction product (III) obtainable according to the inventive method or the inventive reaction product (III) (i.e. the (chemical) product or product mixture) may comprise one or more polyol esters, especially polyglycerol esters, of optionally acylated 3-hydroxybutyric acid of the general formula (IIIa)

(IIIa)

wherein, in the general formula (IIIa),
X represents an organic radical, especially a preferentially saturated organic radical comprising 4 to 20 carbon atoms and optionally comprising 1 to 9 oxygen atoms, preferentially selected from an alkyl radical or a (poly)alkyl ether radical, especially a (poly)alkylene glycol radical, more preferably selected from a $C_4$-$C_{20}$-alkyl radical or a $C_4$-$C_{20}$-(poly)alkyl ether radical, especially a $C_4$-$C_{20}$-(poly)alkylene glycol radical,
the variables m and n, each independently of one another, represent an integer from 1 to 10, R², independently of one another, represents: hydrogen, a radical $CH_3$—$CH(OH)$—$CH_2$—$C(O)$— or a radical $CH_3$—$CH(OR^1)$—$CH_2$—$C(O)$— with $R^1$=acyl group selected from $C(O)$—$CH_3$ (acetyl group) or $C(O)$—$C_2H_5$ (propionyl group), preferably —$C(O)$—$CH_3$ (acetyl group), however, with the proviso that at least one radical R², especially at least two radicals R², does not represent hydrogen, and/or with the proviso that at least one radical R², especially at least two radicals R², represents a radical $CH_3$—$CH(OH)$—$CH_2$—$C(O)$— or a radical $CH_3$—$CH(OR^1)$—$CH_2$—$C(O)$— with $R^1$ as defined hereinabove.

Especially, the groups R²O— can be in any position of the radical X (preferentially wherein at least one group R²O— is terminal).

Especially, in this context, according to a particular embodiment, in the general formula (IIIa), R², independently of one another, may represent hydrogen or a radical $CH_3$—$CH(OH)$—$CH_2$—$C(O)$—, however, with the proviso that at least one radical R², especially at least two radicals R², does not represent hydrogen and/or with the proviso that at least one radical R², especially at least two radicals R², represents a radical $CH_3$—$CH(OH)$—$CH_2$—$C(O)$—.

Furthermore, according to another particular embodiment, in the general formula (IIIa), R², independently of one another, may represent hydrogen or a radical $CH_3$—$CH(OR^1)$—$CH_2$—$C(O)$— with $R^1$ as defined hereinabove, however, with the proviso that at least one radical R², especially at least two radicals R², does not represent hydrogen and/or with the proviso that at least one radical R², especially at least two radicals R², represents a radical $CH_3$—$CH(OR^1)$—$CH_2$—$C(O)$— with $R^1$ as defined hereinabove.

Furthermore, according to yet another particular embodiment, in the general formula (IIIa), R², independently of one another, may represent: a radical $CH_3$—$CH(OH)$—$CH_2$—$C(O)$— or a radical $CH_3$—$CH(OR^1)$—$C(O)$— with $R^1$ as defined hereinabove.

Especially, the reaction product (III) may comprise one or more polyol esters, especially polyglycerol esters, of optionally acylated 3-hydroxybutyric acid of the general formula (IIIb)

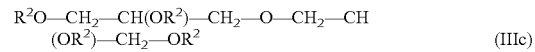

wherein, in the general formula (IIIb),
the variable p represents an integer from 1 to 4, especially 1 or 2, preferentially 1,
R², independently of one another, represents: hydrogen, a radical $CH_3$—$CH(OH)$—$CH_2$—$C(O)$— or a radical $CH_3$—$CH(OR^1)$—$CH_2$—$C(O)$— with $R^1$=acyl group selected from —$C(O)$—$CH_3$ (acetyl group) or —$C(O)$—$C_2H_5$ (propionyl group), preferably —$C(O)$—$CH_3$ (acetyl group), however, with the proviso that at least one radical R², especially at least two radicals R², does not represent hydrogen, and/or with the proviso that at least one radical R², especially at least two radicals R², represents a radical $CH_3$—$CH(OH)$—$CH_2$—$C(O)$— or a radical $CH_3$—$CH(OR^1)$—$CH_2$—$C(O)$— with $R^1$ as defined hereinabove.

Especially, according to a particular embodiment in this context, in the general formula (IIIb), R², independently of one another, may represent hydrogen or a radical $CH_3$—$CH(OH)$—$CH_2$—$C(O)$—, however, with the proviso that at least one radical R², especially at least two radicals R², does not represent hydrogen and/or with the proviso that at least one radical R², especially at least two radicals R², represents a radical $CH_3$—$CH(OH)$—$CH_2$—$C(O)$—.

Furthermore, according to another particular embodiment, in the general formula (IIIb), R², independently of one another, may represent hydrogen or a radical $CH_3$—$CH(OR^1)$—$CH_2$—$C(O)$— with $R^1$ as defined hereinabove, however, with the proviso that at least one radical R², especially at least two radicals R², does not represent hydrogen and/or with the proviso that at least one radical R², especially at least two radicals R², represents a radical $CH_3$—$CH(OR^1)$—$CH_2$—$C(O)$— with $R^1$ as defined hereinabove.

Furthermore, according to yet another particular embodiment, in the general formula (IIIb), R², independently of one another, may represent: a radical $CH_3$—$CH(OH)$—$CH_2$—$C(O)$— or a radical $CH_3$—$CH(OR^1)$—$CH_2$—$C(O)$— with $R^1$ as defined hereinabove.

According to a particular embodiment of the present invention, the reaction product (III) may comprise one or more polyol esters, especially polyglycerol esters, of optionally acylated 3-hydroxybutyric acid of the general formula (IIIc)

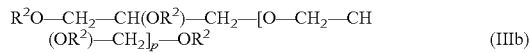

wherein, in the general formula (IIIc), R², independently of each other represents: hydrogen, a radical $CH_3$—$CH(OH)$—$CH_2$—$C(O)$— or a radical $CH_3$—$CH(OR^1)$—$CH_2$—$C(O)$— with $R^1$=acyl group selected from —$C(O)$—$CH_3$ (acetyl group) or —$C(O)$—$C_2H_5$ (propionyl group), preferably —$C(O)$—$CH_3$ (acetyl group), however, with the proviso that at least one radical R², especially at least two radicals R², does not represent hydrogen, and/or with the proviso that at least one radical R², especially at least two radicals R², represents a radical $CH_3$—$CH(OH)$—$CH_2$—$C(O)$— or a radical $CH_3$—$CH(OR^1)$—$CH_2$—$C(O)$— with $R^1$ as defined hereinabove.

Especially, according to a particular embodiment in this context, in the general formula (IIIc), R², independently of one another, may represent hydrogen or a radical $CH_3$—$CH(OH)$—$CH_2$—$C(O)$—, however, with the proviso that at least one radical R², especially at least two radicals R², does not represent hydrogen and/or with the proviso that at least one radical R², especially at least two radicals R², represents a radical $CH_3$—$CH(OH)$—$CH_2$—$C(O)$—.

Furthermore, according to another particular embodiment, in the general formula (IIIc), R², independently of one another, may represent hydrogen or a radical $CH_3$—$CH(OR^1)$—$CH_2$—$C(O)$— with $R^1$ as defined hereinabove, however, with the proviso that at least one radical R², especially at least two radicals R², does not represent hydrogen and/or with the proviso that at least one radical R², especially at least two radicals R², represents a radical $CH_3$—$CH(OR^1)$—$CH_2$—$C(O)$— with $R^1$ as defined hereinabove.

Furthermore, according to yet another particular embodiment, in the general formula (IIIc), R², independently of one another, may represent: a radical $CH_3$—$CH(OH)$—$CH_2$—$C(O)$— or a radical $CH_3$—$CH(OR^1)$—$CH_2$—$C(O)$— with $R^1$ as defined hereinabove.

According to a further particular embodiment, the reaction product (III) may especially comprise a mixture of at least two different polyol esters, especially polyglycerol esters, of optionally acylated 3-hydroxybutyric acid, especially as defined hereinabove (i.e. as a reaction product (III), a mixture of at least two different polyol esters, especially polyglycerol esters, of optionally acylated 3-hydroxybutyric acid, especially as defined hereinabove, is obtained).

According to a further particular embodiment, the reaction product (III) may especially comprise a mixture of at least three different polyol esters, especially polyglycerol esters, of optionally acylated 3-hydroxybutyric acid, especially as defined hereinabove (i.e. as a reaction product (III), a mixture of at least three different polyol esters, especially polyglycerol esters, of optionally acylated 3-hydroxybutyric acid, especially as defined hereinabove, is obtained).

A subject-matter of the present invention is also a polyol ester, especially polyglycerol ester, of optionally acylated 3-hydroxybutyric acid, especially a polyol ester as defined hereinabove,
wherein the polyol ester corresponds to the general formula (IIIa)

(IIIa)

wherein, in the general formula (IIIa),
X represents an organic radical, especially a preferentially saturated organic radical comprising 4 to 20 carbon atoms and optionally comprising 1 to 9 oxygen atoms, preferentially selected from an alkyl radical or a (poly)alkyl ether radical, especially a (poly)alkylene glycol radical, more preferably selected from a $C_4$-$C_{20}$-alkyl radical or a $C_4$-$C_{20}$-(poly)alkyl ether radical, especially a $C_4$-$C_{20}$-(poly)alkylene glycol radical, the variables in and n, each independently of one another, represent an integer from 1 to 10,
$R^2$, independently of one another, represents: hydrogen, a radical $CH_3$—$CH(OH)$—$CH_2$—$C(O)$— or a radical $CH_3$—$CH(OR^1)$—$CH_2$—$C(O)$— with $R^1$=acyl group selected from $C(O)$—$CH_3$ (acetyl group) or $C$—$(O)$—$C_2H_5$ (propionyl group), preferably —$C(O)$—$CH_3$ (acetyl group), however, with the proviso that at least one radical $R^2$, especially at least two radicals $R^2$, does not represent hydrogen, and/or with the proviso that at least one radical $R^2$, especially at least two radicals $R^2$, represents a radical $CH_3$—$CH(OH)$—$CH_2$—$C(O)$— or a radical $CH_3$—$CH(OR^1)$—$CH_2$—$C(O)$— with $R^1$ as defined hereinabove.

Especially the groups $R^2O$— can be in any position of the radical X (preferentially wherein at least one group $R^2O$— is terminal).

Especially, according to a particular embodiment, in the general formula (IIIa), $R^2$, independently of one another, may represent hydrogen or a radical $CH_3$—$CH(OH)$—$CH_2$—$C(O)$—, however, with the proviso that at least one radical $R^2$, especially at least two radicals $R^2$, does not represent hydrogen and/or with the proviso that at least one radical $R^2$, especially at least two radicals $R^2$, represents a radical $CH_3$—$CH(OH)$—$CH_2$—$C(O)$—.

Furthermore, according to another particular embodiment, in the general formula (IIIa), $R^2$, independently of one another, may represent hydrogen or a radical $CH_3$—$CH(OR^1)$—$CH_2$—$C(O)$— with $R^1$ as defined hereinabove, however, with the proviso that at least one radical $R^2$, especially at least two radicals $R^2$, does not represent hydrogen and/or with the proviso that at least one radical $R^2$, especially at least two radicals $R^2$, represents a radical $CH_3$—$CH(OR^1)$—$CH_2$—$C(O)$— with $R^1$ as defined hereinabove.

Furthermore, according to yet another particular embodiment, in the general formula (IIIa), $R^2$, independently of one another, may represent: a radical $CH_3$—$CH(OH)$ $CH_2$—$C(O)$— or a radical $CH_3$—$CH(OR^1)$—$CH_2$—$C(O)$— with $R^1$ as defined hereinabove.

A further object of the present invention is also a polyol ester, especially polyglycerol ester, of optionally acylated 3-hydroxy-butyric acid, especially a polyol ester as defined hereinabove,
wherein the polyol ester corresponds to the general formula (IIIb)

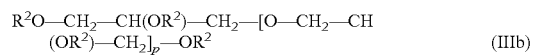

(IIIb)

wherein, in the general formula (IIIb),
the variable p represents an integer from 1 to 4, especially 1 or 2, preferentially 1,
$R^2$, independently of each other, represents: hydrogen, a radical $CH_3$—$CH(OH)$—$CH_2$—$C(O)$— or a radical $CH_3$—$CH(OR^1)$—$CH_2$—$C(O)$— with $R^1$ acyl group selected from —$C(O)$—$CH_3$ (acetyl group) or —$C(O)$—$C_2H_5$ (propionyl group), preferably —$C(O)$—$CH_3$ (acetyl group), however, with the proviso that at least one radical $R^2$, especially at least two radicals $R^2$, does not represent hydrogen, and/or with the proviso that at least one radical $R^2$, especially at least two radicals $R^2$, represents a radical $CH_3$—$CH(OH)$—$CH_2$—$C(O)$— or a radical $CH_3$—$CH(OR^1)$—$CH_2$—$C(O)$— with $R^1$ as defined hereinabove.

Especially, according to a particular embodiment, in the general formula (IIIb), $R^2$, independently of one another, may represent hydrogen or a radical $CH_3$—$CH(OH)$—$CH_2$—$C(O)$—, however, with the proviso that at least one radical $R^2$, especially at least two radicals $R^2$, does not represent hydrogen and/or with the proviso that at least one radical $R^2$, especially at least two radicals $R^2$, represents a radical $CH_3$—$CH(OH)$—$CH_2$—$C(O)$—.

Furthermore, according to another particular embodiment, in the general formula (IIIb), $R^2$, independently of one another, may represent hydrogen or a radical $CH_3$—$CH(OR^1)$—$CH_2$—$C(O)$— with $R^1$ as defined hereinabove, however, with the proviso that at least one radical $R^2$, especially at least two radicals $R^2$, does not represent hydrogen and/or with the proviso that at least one radical $R^2$, especially at least two radicals $R^2$, represents a radical $CH_3$—$CH(OR^1)$—$CH_2$—$C(O)$— with $R^1$ as defined hereinabove.

Furthermore, according to yet another particular embodiment, in the general formula (IIIb), $R^2$, independently of one another, may represent: a radical $CH_3$—$CH(OH)$—$CH_2$—$C(O)$— or a radical $CH_3$—$CH(OR^1)$—$CH_2$—$C(O)$— with $R^1$ as defined hereinabove.

Again, another object of the present invention is also a polyol ester, especially polyglycerol ester, of optionally acylated 3-thydroxybutyric acid, especially a polyol ester as defined hereinabove,
wherein the polyol ester corresponds to the general formula (IIIc)

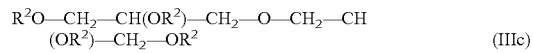

(IIIc)

wherein, in the general formula (IIIc), $R^2$, independently of one another, represents: hydrogen, a radical $CH_3$—$CH(OH)$—$CH_2$—$C(O)$— or a radical $CH_3$—$CH(OR^1)$—$CH_2$—$C(O)$— with $R^1$=acyl group selected from —$C(O)$—$CH_3$ (acetyl group) or —$C(O)$—$C_2H_5$ (propionyl group), preferably —$C(O)$—$CH_3$ (acetyl group), however, with the proviso that at least one radical $R^2$, especially at least two radicals $R^2$, does not represent hydrogen, and/or with the proviso that at least one radical $R^2$, especially at least two radicals $R^2$, represents a radical $CH_3$—$CH(OH)$—$CH_2$—$C(O)$— or a radical $CH_3$—$CH(OR^1)$—$CH_2$—$C(O)$— with $R^1$ as defined hereinabove.

Especially, according to a particular embodiment, in the general formula (IIIc), $R^2$, independently of one another, may represent hydrogen or a radical $CH_3$—$CH(OH)$—$CH_2$—$C(O)$—, however, with the proviso that at least one radical $R^2$, especially at least two radicals $R^2$, does not represent hydrogen and/or with the proviso that at least one radical $R^2$, especially at least two radicals $R^2$, represents a radical $CH_3$—$CH(OH)$—$CH_2$—$C(O)$—.

Furthermore, according to another particular embodiment, in the general formula (IIIc), $R^2$, independently of one another, may represent hydrogen or a radical $CH_3$—$CH(OR^1)$—$CH_2$—$C(O)$— with $R^1$ as defined hereinabove, however, with the proviso that at least one radical $R^2$, especially at least two radicals $R^2$, does not represent hydrogen and/or with the proviso that at least one radical $R^2$, especially at least two radicals $R^2$, represents a radical $CH_3$—$CH(OR^1)$—$CH_2$—$C(O)$— with $R^1$ as defined hereinabove.

Furthermore, according to yet another particular embodiment, in the general formula (IIIc), $R^2$, independently of one another, may represent: a radical $CH_3$—$CH(OH)$—$CH_2$—$C(O)$— or a radical $CH_3$—$CH(OR^1)$—$CH_2$—$C(O)$— with $R^1$ as defined hereinabove.

A further object of the present invention according to this aspect of the invention is, according to a particular embodiment, a mixture comprising at least two different polyol esters, especially polyglycerol esters, of optionally acylated 3-hydroxybutyric acid, as defined hereinabove.

Again, another object of the present invention according to this aspect of the invention is, according to another particular embodiment, a mixture comprising at least three different polyol esters, especially polyglycerol esters, of optionally acylated 3-hydroxybutyric acid, as defined hereinabove.

The reaction product obtainable according to the inventive method or the inventive reaction product as defined hereinabove, respectively, and/or the polyol ester, especially polyglycerol ester, of optionally acylated 3-hydroxybutyric acid obtainable according to the inventive production method or the inventive polyol ester, especially polyglycerol ester, of optionally acylated 3-hydroxybutyric acid, as defined hereinabove, respectively, and/or the mixture, obtainable according to the inventive production method or the inventive mixture as defined hereinabove, respectively, comprises a multitude of advantages and special features compared to the prior art:

As the applicant has surprisingly found out, the reaction product obtainable according to the inventive method or the inventive reaction product as defined hereinabove, respectively, and/or the polyol ester, especially polyglycerol ester, of optionally acylated 3-hydroxybutyric acid obtainable according to the inventive production method or the inventive polyol ester, especially polyglycerol ester, of optionally acylated 3-hydroxybutyric acid, as defined hereinabove, respectively, and/or the mixture obtainable according to the inventive production method or the inventive mixture as defined hereinabove, respectively, is suitable as a precursor or metabolite of 3-hydroxybutyric acid or its salts, since, on the one hand, it is converted physiologically, especially in the gastrointestinal tract, to 3-hydroxybutyric acid or its salts and, on the other hand, it simultaneously comprises a good physiological compatibility or tolerability, especially with regard to non-toxicity and acceptable organoleptic properties.

Moreover, the reaction product obtainable according to the inventive method or the inventive reaction product as defined hereinabove, respectively, and/or the polyol ester, especially polyglycerol ester, of optionally acylated 3-hydroxybutyric acid obtainable according to the inventive production method or the inventive polyol ester, especially polyglycerol ester, of optionally acylated 3-hydroxybutyric acid, as defined hereinabove, respectively, and/or the mixture obtainable according to the inventive production method or the inventive mixture as defined hereinabove, respectively, is easily accessible or available on a large scale on a synthetic basis, even on a commercial scale, and with the required pharmaceutical or pharmacological quality, Additionally, the reaction product obtainable according to the inventive method or the inventive reaction product as defined hereinabove, respectively, and/or the polyol ester, especially polyglycerol ester, of optionally acylated 3-hydroxybutyric acid obtainable according to the inventive production method or the inventive polyol ester, especially polyglycerol ester, of optionally acylated 3-hydroxybutyric acid, as defined hereinabove, respectively, and/or the mixture obtainable according to the inventive production method or the inventive mixture as defined hereinabove, respectively, can, if necessary, be provided in enantiomerically pure or enantiomerically enriched form.

The reaction product obtainable according to the inventive method or the inventive reaction product as defined hereinabove, respectively, and/or the polyol ester, especially polyglycerol ester, of optionally acylated 3-hydroxybutyric acid obtainable according to the inventive production method or the inventive polyol ester, especially polyglycerol ester, of optionally acylated 3-hydroxybutyric acid, as defined hereinabove, respectively, and/or the mixture obtainable according to the inventive production method or the inventive mixture as defined hereinabove, respectively, thus represents an efficient pharmacological drug target in the context of keto-body therapy of the human or animal body.

In the following, the remaining aspects of the invention are explained in more detail.

A further subject-matter of the present invention—according to a third aspect of the present invention—is a pharmaceutical composition, especially a drug or medicament, which comprises a reaction product obtainable according to the inventive production method or the inventive reaction product as defined hereinabove, respectively, and/or a polyol ester, especially polyglycerol ester, of optionally acylated 3-hydroxybutyric acid obtainable according to the inventive production method or the inventive polyol ester, especially polyglycerol ester, of optionally acylated 3-hydroxybutyric acid, as defined hereinabove, respectively, and/or a mixture obtainable according to the inventive production method or the inventive mixture as defined hereinabove, respectively.

Especially, according to this aspect of the invention, the present invention relates to a pharmaceutical composition for the prophylactic and/or therapeutic treatment or for use in the prophylactic and/or therapeutic treatment of diseases of the human or animal body. This may especially concern diseases associated with a disorder of the energy metabolism, especially keto-body metabolism, such as especially craniocerebral trauma, stroke, hypoxia, cardiovascular diseases such as myocardial infarction, refeeding syndrome, anorexia, epilepsy, neurodegenerative diseases such as dementia, Alzheimer's disease, Parkinson's disease, multiple sclerosis and amyotrophic lateral sclerosis, fat metabolic diseases such as glucose transporter defect (GLUT1 defect), VL-FAOD and mitochondriopathies such as mitochondrial thiolase defect, Huntington's disease, cancers such as T-cell lymphomas, astrocytomas and glioblastomas, HIV, rheumatic diseases such as rheumatoid arthritis and arthritis urica, diseases of the gastrointestinal tract such as chronic inflammatory bowel diseases, especially ulcerative colitis and Crohn's disease, lyosomal storage diseases such as sphingolipidosis, especially Niemann-Pick disease, diabetes mellitus and effects or side-effects of chemotherapy.

Again, a further subject matter of the present invention—according to a fourth aspect of the present invention—is a reaction product obtainable according to the inventive production method or the inventive reaction product as defined hereinabove, respectively, and/or a polyol ester, especially polyglycerol ester, of optionally acylated 3-hydroxbutyric acid obtainable according to the inventive production method or the inventive polyol ester, especially polyglycerol ester, of optionally acylated 3-hydroxbutyric acid, as defined hereinabove, respectively, and/or a mixture obtainable according to the inventive production method or the inventive mixture as defined hereinabove, respectively, for the prophylactic and/or therapeutic treatment or for use in the prophylactic and/or therapeutic treatment of diseases of the human or animal body, especially diseases associated with a disorder of the energy metabolism, especially keto-body metabolism, such as especially craniocerebral trauma, stroke, hypoxia, cardiovascular diseases such as myocardial infarction, refeeding syndrome, anorexia, epilepsy, neurodegenerative diseases such as dementia, Alzheimer's disease, Parkinson's disease, multiple sclerosis and amyotrophic lateral sclerosis, fat metabolic diseases such as glucose transporter defect (GLUT1 defect), VL-FAOD and mitochondriopathies such as mitochondrial thiolase defect, Huntington's disease, cancers such as T-cell lymphomas, astrocytomas and glioblastomas, HIV, rheumatic diseases such as rheumatoid arthritis and arthritis urica, diseases of the gastrointestinal tract such as chronic inflammatory bowel diseases, especially ulcerative colitis and Crohn's disease, lyosomal storage diseases such as sphingolipidosis, especially Niemann-Pick disease, diabetes mellitus and effects or side-effects of chemotherapy.

Likewise, a further subject-matter of the present invention—according to a fifth aspect of the present invention—is the use of a reaction product obtainable according to the inventive production method or the inventive reaction product as defined hereinabove, respectively, and/or a polyol ester, especially polyglycerol ester, of optionally acylated 3-hydroxbutyric acid obtainable according to the inventive production method or the inventive polyol ester, especially polyglycerol ester, of optionally acylated 3-hydroxbutyric acid, as defined hereinabove, respectively, and/or a mixture obtainable according to the inventive production method or the inventive mixture as defined hereinabove, respectively, for the prophylactic and/or therapeutic treatment or for producing a pharmaceutical for the prophylactic and/or therapeutic treatment of diseases of the human or animal body, especially diseases associated with a disorder of the energy metabolism, especially keto-body metabolism, such as especially craniocerebral trauma, stroke, hypoxia, cardiovascular diseases such as myocardial infarction, refeeding syndrome, anorexia, epilepsy, neurodegenerative diseases such as dementia, Alzheimer's disease, Parkinson's disease, multiple sclerosis and amyotrophic lateral sclerosis, fat metabolic diseases such as glucose transporter defect (GLUT1 defect), VL-FAOD and mitochondriopathies such as mitochondrial thiolase defect, Huntington's disease, cancers such as T-cell lymphomas, astrocytomas and glioblastomas, HIV, rheumatic diseases such as rheumatoid arthritis and arthritis urica, diseases of the gastrointestinal tract such as chronic inflammatory bowel diseases, especially ulcerative colitis and Crohn's disease, lyosomal storage diseases such as sphingolipidosis, especially Niemann-Pick disease, diabetes mellitus and effects or side-effects of chemotherapy.

Likewise, a further subject-matter of the present invention—according to as sixth aspect of the present invention—is the use of a reaction product obtainable according to the inventive production method or the inventive reaction product as defined hereinabove, respectively, and/or a polyol ester, especially polyglycerol ester, of optionally acylated 3-hydroxbutyric acid obtainable according to the inventive production method or the inventive polyol ester, especially polyglycerol ester, of optionally acylated 3-hydroxbutyric acid, as defined hereinabove, respectively, and/or a mixture obtainable according to the inventive production method or the inventive mixture as defined hereinabove, respectively, for the prophylactic and/or therapeutic treatment or for producing a medicament for the prophylactic and/or therapeutic treatment of or for the application for catabolic metabolic states, such as hunger, diets or low-carbohydrate nutrition.

Likewise, a further subject-matter of the present invention—according to a seventh aspect of the present invention—is a food and/or a food product, which comprises a reaction product obtainable according to the inventive production method or the inventive reaction product as defined hereinabove, respectively, and/or a polyol ester, especially polyglycerol ester, of optionally acylated 3-hydroxbutyric acid obtainable according to the inventive production method or the inventive polyol ester, especially polyglycerol ester, of optionally acylated 3-hydroxbutyric acid, as defined hereinabove, respectively, and/or a mixture obtainable according to the inventive production method or the inventive mixture as defined hereinabove, respectively.

According to a particular embodiment, the food and/or the food product may essentially be a dietary supplement, a functional food, a novel food, a food additive, a food supplement, a dietary food, a power snack, an appetite suppressant or a strength and/or endurance sport supplement.

Finally, yet another subject-matter of the present invention—according to an eighth aspect of the present invention—is the use of a reaction product obtainable according to the inventive production method or the inventive reaction product as defined hereinabove, respectively, and/or a polyol ester, especially polyglycerol ester, of optionally acylated 3-hydroxbutyric acid obtainable according to the inventive production method or the inventive polyol ester, especially polyglycerol ester, of optionally acylated 3-hydroxbutyric acid, as defined hereinabove, respectively, and/or a mixture obtainable according to the inventive production method, as defined hereinabove, in a food and/or a food product.

According to this aspect of the invention, the food and/or the food product may especially be a dietary supplement, a functional food, a novel food, a food additive, a food supplement, a dietary food, a power snack, an appetite suppressant or a strength and/or endurance sports supplement.

Further embodiments, modifications and variations of the present invention are readily recognizable or realizable by a person skilled in the art when reading the description, without leaving the scope of the present invention.

The present invention is illustrated by the following examples, which are not intended to limit the present invention in any way, but only to explain the exemplary and non-limiting implementation and configuration of the present invention.

EXAMPLES

Abbreviations Used

BHB=3-BHB=3-hydroxybutyric acid
PG(2)=diglycerol: HO—CH$_2$—CH(OH)—CH$_2$—O—CH$_2$—CH(OH)—CH$_2$—OH
PG(3)=polyglycerol: HO—CH$_2$—CH(OH)—CH$_2$—[O—CH$_2$—CH(OH)—CH$_2$]$_2$—OH Examples of Production The inventive production method is illustrated by the following examples. The relevant general reaction scheme is shown and explained in the general description section Example 1

Production of 3-acetoxy-BHB-diglycerol Mixtures from Diglycerol and Acetylated 3-hydroxybutyric acid anhydride (=3-acetoxybutyric acid anhydride) with Subsequent Hydrolysis of the Acetyl Groups In a 1,000 ml multi-neck flask with dephiegmator (partial condenser) and distillation bridge 25 g (R)/(S)-3-hydroxybutyric acid are added to 95 g acetic add. 90 g acetic anhydride are added to the reaction mixture at 80° C. under N$_2$-atmosphere within one hour. The reaction mixture is stirred at 80° C. for another 4 to 5 hours. 3-Acetoxybutyric anhydride (=acetylated 3-hydroxybutyric anhydride) is formed.

Then 3.5 g diglycerol are added to the reaction mixture at 80° C. and stirred for 8 to 10 hours. The reaction product is a mixture of diglycerol esters of 3-acetoxybutyric acid (i.e. in other words, a mixture of diglycerol esters of acetylated 3-hydroxybutyric acid).

The by-products formed (acetic acid from the first stage and 3-acetoxybutyric acid from the second stage) are distilled off under vacuum (<50 mbar) at 100 to 120° C. Characterization is performed by GC, GPC and GC-MS.

Part of the reaction product (i.e. mixture of diglycerol esters of the 3-acetoxybutyric acids) is then subjected to hydrolysis of the acetyl groups (partial or selective hydrolysis in the presence of an enzyme). For this purpose, the reaction product is reacted in aqueous medium in the presence of immobilized enzyme (CALB lipase on polymer support, derived from *Candida antarctica*, first preparation: Novozym® 435 from Sigma-Aldrich or Merck and second preparation: Lipozym® 435 from Strem Chemicals, Inc.) for 8 hours at 50° C. After separation of the enzyme and subsequent purification by distillation, a mixture of diglycerol esters of 3-hydroxybutyric add is obtained as the hydrolysis product. Characterization is performed by GC, GPC and GC-MS.

Part of the obtained mixture of diglycerol esters of 3-hydroxybutyric acid is chromatographically separated into the individual diglycerol esters (i.e. mono-diglycerol ester, di-diglycerol ester, tri-diglycerol ester, etc.) and the individual diglycerol esters are each obtained as pure substances.

Example 2

Further Production of 3-acetyl-BHB-diglycerol Mixtures from Diglycerol and Acetylated 3-hydroxybutyric anhydride (=3-acetoxybutyric anhydride) with Subsequent Hydrolysis of the Acetyl Groups Example 1 is repeated, however, after the reaction of (R)/(S)-3hydroxybutyric anhydride the by-product formed (acetic acid) is removed by distillation under vacuum (<50 mbar) at 100 to 120° C., to obtain 3-acetoxybutyric anhydride. Characterization is performed by GC, GPC and GC-MS.

Subsequently, the pure 3-acetoxybutyric anhydride is reacted with diglycerol, purified and analyzed (as described in Example 1) to yield a pure mixture of diglycerol esters of 3-acetoxybutyric acid.

A portion of the reaction product (i.e. mixture of diglycerol esters of 3-acetoxybutyric acid) is then hydrolyzed as described in Example 1 to yield a mixture of diglycerol esters of 3-hydroxybutyric acid. Characterization is performed by GC, GPC and GC-MS.

Part of the obtained mixture of diglycerol esters of 3-hydroxybutyric acid is chromatographically separated into the individual diglycerol esters (i.e. mono-diglycerol ester, di-diglycerol ester, tri-diglycerol ester, etc.) and the individual diglycerol esters are each obtained as pure substances.

Example 3

Further Production of 3-acetyl-BHB-diglycerol Mixtures from Diglycerol and Acetylated 3-hydroxybutyric anhydride (=3-acetoxybutyric anhydride) with Subsequent Hydrolysis of the Acetyl Groups In a 5,000-ml-multi-neck flask with dephlegmator (partial condenser) and distillation bridge 250 g (R)/(S)-3-hydroxybutyric acid are added to 950 g acetic acid. 900 g acetic anhydride are added to the reaction mixture at 80° C. under N$_2$-atmosphere within one hour. The reaction mixture is stirred at 80° C. for another 4 to 5 hours. 3-Acetoxybutyric anhydride (=acetylated 3-hydroxybutyric anhydride) is formed. The by-product formed (acetic acid) is removed by distillation under vacuum (<50 mbar) at 100 to 120° C. to obtain pure 3-acetoxybutyric anhydride. Characterization is performed by GC, GPC and GC-MS.

Then, 35 g diglycerol are added to the purified 3-acetoxybutyric anhydride at 80° C. and stirred for 8 to 10 hours. The reaction product is a mixture of diglycerol esters of 3-acetoxybutyric acid (i.e. in other words, a mixture of diglycerol esters of acetylated 3-hydroxybutyric acid).

The by-product formed (3-acetoxybutyric acid) is distilled off under vacuum (<50 mbar) at 100 to 120° C. Characterization is performed by GC, GPC and GC-MS.

Part of the reaction product (i.e, mixture of diglycerol esters of the 3-acetoxybutyric acids) is then subjected to hydrolysis of the acetyl groups (partial or selective hydrolysis in the presence of enzyme). For this purpose, the reaction product is reacted in aqueous medium in the presence of immobilized enzyme (CALB lipase on polymer support, derived from *Candida antarctica*, first preparation: Novozym® 435 from Sigma-Aldrich or Merck and second preparation: Lipozym® 435 from Strem Chemicals, Inc.) for 8 hours at 50° C. After separation of the enzyme and subsequent purification by distillation, a mixture of diglycerol esters of 3-hydroxybutyric acid is obtained as the hydrolysis product. Characterization is performed b GC, GPC and GC-MS.

Part of the obtained mixture of diglycerol esters of 3-hydroxybutyric acid is chromatographically separated into the individual diglycerol esters i.e. mono-diglycerol ester, di-diglycerol ester, tri-diglycerol ester, etc.) and the individual diglycerol esters are each obtained as pure substances.

Further Production of 3-BHB-Diglycerol Ester Mixtures

The three preceding experiments are each repeated, however, with different polyols (namely each with polyglycerol PG(3) and with 1,2-pentanediol).

The aforementioned polyalcohols 1,2-pentanediol and polyglycerol PG(3) are autocatalytically converted efficiently to the desired products. Comparable results to the previous experiments are obtained. Purification, separation or fractionation and hydrolysis are carried out in the same way.

The experiments with 1,2-pentanediol, diglycerol and polyglycerol PG(3) are repeated using sulfuric acid ($H_2SO_4$) as a catalyst and at temperatures between 75 and 110° C. Comparable results are obtained. Purification, separation or fractionation and hydrolysis are carried out in the same way.

The experiments with 1,2-pentanediol, diglycerol and polyglycerol PG(3) are repeated using hydrochloric acid (HCl) as a catalyst and at temperatures between 75 and 110° C. Comparable results are obtained. Purification, separation or fractionation and hydrolysis are carried out in the same way.

The experiments with 1,2-pentanediol, diglycerol and polyglycerol PG(3) are repeated using phosphoric acid ($H_3PO_4$) as a catalyst and at temperatures between 75 and 110° C. Comparable results are obtained. Purification, separation or fractionation and hydrolysis are carried out in the same way.

Since especially the 3-BHB diglycerol esters have only a slightly bitter taste, these esters in particular are an efficient product group for therapeutic application. Therefore, the preceding experiment is carried out autocatalytically and with diglycerol as polyalcohol on a larger scale (2 to 4 kg).

First, the stoichiometric reaction conditions of the previous experiments are applied on a scale of 2 kg (40 mol-% excess 3-acetoxybutyric anhydride). After 15 h, a portion of the reaction mixture (about 200 g) is removed for further analysis. This is a mono/di-diglycerol ester mixture. Then another approx. 2 kg 3-acetoxybutyric anhydride are added. The amount corresponds to an excess of 100 mol-%, already calculated on the (R)-enantiomer. The goal is to produce a full ester. It can be seen that after about 20 to 30 h, a constant content of di-PG(2) ester is obtained; the mono-diglycerol ester content decreases and the tri-diglycerol ester content increases. Further analyses (GPC) show that a tetra-diglycerol ester was also formed.

After distillation of excess 3-acetoxybutyric acid, hydrolysis of the acetyl groups (partial or selective hydrolysis in the presence of enzyme) is carried out in aqueous medium in the presence of an immobilized enzyme (CALB lipase on polymer support, derived from *Candida antarctica*, first preparation: Novozym® 435 from Sigma-Aldrich or Merck and second preparation: Lipozym® 435 from Strem Chemicals, Inc.) for 8 hours at 50° C. After separation of the enzyme and subsequent purification by distillation, a mixture of diglycerol esters of 3-hydroxybutyric acid is obtained as the hydrolysis product. The mixture of diglycerol esters of 3hydroxybutyric acid has only a slightly bitter taste and is organoleptically acceptable and compatible.

Functionalization Experiments

The mono-/di-/tri-/tetra-diglycerol ester mixtures or their acylated derivatives obtained in the preceding experiments and the individual diglycerol esters in pure form or their acylated analogs separated chromatographically therefrom are each subsequently functionalized by reaction with $C_7$-anhydride to obtain products completely esterified at all the remaining, i.e. still free, OH-groups. The general reaction scheme for this is shown and explained in the general description section.

The experiments show that the intended functionalization by reaction with $C_7$-anhydride leads to the desired products (i.e, esterification of the free OH-groups), as confirmed by appropriate analysis.

Comparable functionalization experiments are also carried out with higher carboxylic acid anhydrides (each with $C_{10}$-, $C_{20}$- and $C_{28}$-carboxylic acid anhydrides) and lead to analogous results (i.e. esterification of the free OH-groups), as confirmed by corresponding analysis.

Further Functionalization Attempts

The mono-/di-/tri-/tetra-diglycerol ester mixtures or their acylated derivatives obtained in the preceding experiments and the individual diglycerol esters in pure form or their acylated analogs separated chromatographically therefrom are each subsequently functionalized by reaction with 3-acetoxybutyric anhydride to obtain products completely esterified at all the remaining i.e. still free, OH-groups.

The experiments show that the intended functionalization by reaction with 3-acetoxybutyric anhydride leads to the desired products (i.e. esterification of the free OH-groups), as confirmed by appropriate analysis.

Physiological Application Tests: In-Vitro Digestion Tests

Digestion Experiments (Splitting or Cleavage Experiments) of Inventive 3-BHB-Diglycerol Ester Mixtures By means of cleavage experiments it is shown that 3-BHB-PG(2) esters or their mixtures, including reaction by-products such as dimers etc., produced according to the invention, can be cleaved in the human gastrointestinal tract.

The starting mixture used are:
- a purified mixture of 3-BHB mono-diglycerol ester, 3-BHB di-diglycerol ester, 3-BHB tri-diglycerol ester and 3-BHB tetra-diglycerol ester obtained by the method of the invention (sample 1)
- a purified mixture of mono-diglycerol ester, di-diglycerol ester, tri-diglycerol ester and tetra-diglycerol ester of acylated 3-hydroxybutyric add (=3-acetoxybutyric acid) obtained by the method of the invention (sample 2)
- 3-BHB mono-diglycerol ester (sample 3)
- 3-BHB di-diglycerol ester (sample 4)
- 3-BHB tri-diglycerol ester (sample 5)
- mono-diglycerol ester of acylated 3-hydroxybutyric acid (=3-acetoxybutyric acid) (sample 6).
- di-diglycerol ester of acylated 3-hydroxybutyric acid (=3-acetoxybutyric acid) (sample 7).
- tri-diglycerol ester of acylated 3-hydroxybutyric acid (=3-acetoxybutyric acid) (sample 8).
- $C_7$-anhydride-functionalized mixture of 3-BHB mono-diglycerol ester, 3-BHB di-diglycerol ester, 3-BHB tri-diglycerol ester and 3-BHB tetra-diglycerol ester (sample 9).
- 3-acetoxybutyric anhydride functionalized mixture of 3-BHB mono-diglycerol ester, 3-BHB di-diglycerol ester, 3-BHB tri-diglycerol ester and 3-BHB tetra-diglycerol ester (sample 10).

For the cleavage experiments under near-body conditions two media are investigated:

FaSSGF, which simulates the stomach

FaSSIF, which simulates the intestinal tract

Both media are from the company Biorelevant®, Ltd. in Great Britain. In addition, in some experiments porcine pancreas is added (Panzytrat® 40,000, Fa. Allergan).

The results of the cleavage experiments in a FaSSGF or FaSSIF medium with Panzytrat® and without Panzytrat® (both 35° C., 24 h) show that the samples hydrolyze under FaSSGF conditions with Panzytrat® and without Panzytrat®; this is mainly due to the low pH value (pH=1.6) of the medium, finder FaSSIF conditions, a lower conversion using Panzytrat® takes place.

In all experiments it can be seen that the cascade (tetraester becomes triester, triester becomes diester etc.) continues until the desired free acid 3-BHB or 3-BHB-FS is obtained.

Further Digestion Experiments (Cleavage Experiments) of Inventive 3-BHB-PG(2) Ester Mixtures Cleavage Experiments with Pancreatin 2 g of the samples 1 to 10 described hereinabove are dissolved in 50 g water and 0.5 (1% by weight) pancreatin is added. The pancreatin is used in the form of the commercially available product Panzytrat® 40,000 from the Allergan company. The whole mixture is stirred on a hot plate at 50° C.; the course of the reaction is determined and monitored by continuously recording the acid number over time. The acid number increases over the observation period (cleavage of the 3-BHB-diglycerol ester mixture to the free acid). The conversion/time course of the aqueous cleavage of the mixture of esters according to the invention by means of pancreatin, including the increase in the acid number over time, demonstrates the desired decomposition of the educt mixture to the free acid. This is confirmed by appropriate analysis. The experiment proves that the starting mixture according to the invention is a suitable physiological precursor for 3-hydroxybutyric acid for the corresponding beta-body therapies.

The previously described cleavage experiments prove that the polyol esters, especially polyglycerol esters, of 3-hydroxybutyric acid are efficient precursors or metabolites of free hydroxybutyric acid or its salts, especially with regard to their intended effect, which are present in physiologically compatible or physiologically compatible form.

The invention claimed is:

1. A method for producing polyol esters of at least one of 3-hydroxybutyric acid and acylated 3-hydroxybutyric acid, wherein at least one compound of the general formula (I)

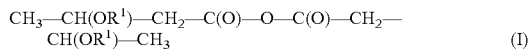

wherein, in the general formula (I), the radical $R^1$ represents an acyl group selected from an acetyl group of formula —C(O)—CH$_3$ and a propionyl group of formula —C(O)—C$_2$H$_5$, is reacted with at least one polyol (II) comprising at least two hydroxyl groups, optionally followed by hydrolysis of the acyl groups, so that, as a reaction product (III), one or more polyol esters of at least one of 3-hydroxybutyric acid and acylated 3-hydroxybutyric acid are obtained.

2. The method according to claim 1,
wherein the reaction of the at least one compound of the general formula (I) with the at least one polyol (II) is followed by hydrolysis of the acyl groups, so that, as a reaction product (III), one or more polyol esters of 3-hydroxybutyric acid are obtained.

3. The method according to claim 1,
wherein the reaction is carried out in the absence of any solvents; and
wherein the reaction is carried out autocatalytically or in the presence of a catalyst.

4. The method according to claim 1,
wherein the compound of the general formula (I) and the polyol (II) are used in a molar ratio of compound of the general formula (I)/polyol (II) in a range of from 1:1 to 10:1.

5. The method according to claim 1,
wherein the polyol (II) comprises at least three hydroxyl groups; and
wherein the polyol (II) corresponds to the general formula (IIa)

wherein, in the general formula (IIa),
X represents an organic radical comprising 4 to 20 carbon atoms and optionally comprising 1 to 9 oxygen atoms; and
the variables m and n, each independently of one another, represent an integer from 1 to 10;
wherein the hydroxyl groups of the polyol (II) are in any position of the radical X,
wherein at least one hydroxyl group is a primary hydroxyl group.

6. The method according to claim 1,
wherein the polyol (II) is selected from polyether polyols of the general formula (IIb)

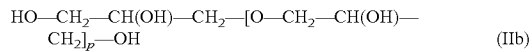

wherein, in the general formula (IIb), the variable p represents an integer from 1 to 4.

7. The method according to claim 1,
wherein hydroxyl groups still present in the reaction product (III) after the reaction has been performed are at least partially esterified, wherein the esterification is carried out by reaction with a carboxylic acid anhydride.

8. A polyol ester of at least one of 3-hydroxy-butyric acid and acylated 3-hydroxy-butyric acid,
wherein the polyol ester corresponds to the general formula (IIIb)

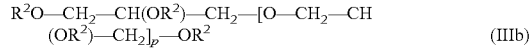

wherein, in the general formula (IIIb),
the variable p represents an integer from 1 to 4,
$R^2$, independently of each other, represents: hydrogen, a radical CH$_3$—CH(OH)—CH$_2$—C(O)— or a radical CH$_3$—CH(OR$^1$)—CH$_2$—C(O)— with $R^1$=acyl group selected from an acetyl group of formula —C(O)—CH$_3$) and a propionyl group of formula —C(O)—C$_2$H$_5$, however, with the proviso that at least one radical $R^2$ represents a radical CH$_3$—CH(OH)—CH$_2$—C(O)— or a radical CH$_3$—CH(OR$^1$)—CH$_2$—C(O)— with $R^1$ as defined hereinabove.

9. The polyol esters according to claim 8,
wherein, in the general formula (IIIb), $R^2$, independently of each other, represents: hydrogen, a radical CH$_3$—CH(OH)—CH$_2$—C(O)— or a radical CH$_3$—CH(OR$^1$)—CH$_2$—C(O)— with $R^1$ acyl group selected from an acetyl group of formula —C(O)—CH$_3$) and a propionyl group of formula —C(O)—C₂H₅, however, with the proviso that at least two radicals R² represent a radical CH₃—CH(OH)—CH₂—C(O)— or a radical CH₃—CH(OR¹)—CH₂—C(O)— with R¹ as defined hereinabove.

10. The polyol esters according to claim 8,
wherein the polyol ester corresponds to the general formula (IIIc)

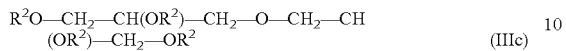

R²O—CH₂—CH(OR²)—CH₂—O—CH₂—CH(OR²)—CH₂—OR²   (IIIc)

wherein, in the general formula (IIIc), R², independently of one another, represents: hydrogen, a radical CH₃—CH(OH)—CH₂—C(O)— or a radical CH₃—CH(OR¹)—CH₂—C(O)— with R¹ acyl group selected from an acetyl group of formula —C(O)—CH₃ and a propionyl group of formula —C(O)—C₂H₅, however, with the proviso that at least one radical R² represents a radical CH₃—CH(OH)—CH₂—C(O)— or a radical CH₃—CH(OR¹)—CH₂—C(O)— with R¹ as defined hereinabove.

11. The polyol esters according to claim 10,
wherein, in the general formula (IIIc), R², independently of one another, represents: hydrogen, a radical CH₃—CH(OH)—CH₂—C(O)— or a radical CH₃—CH(OR¹)—CH₂—C(O)— with R¹ acyl group selected from an acetyl group of formula —C(O)—CH₃ and a propionyl group of formula —C(O)—C₂H₅, however, with the proviso that at least two radicals R² represent a radical CH₃—CH(OH)—CH₂—C(O)— or a radical CH₃—CH(OR¹)—CH₂—C(O)— with R¹ as defined hereinabove.

12. A mixture comprising at least two different polyol esters according to claim 8.

13. A pharmaceutical composition,
wherein the pharmaceutical composition comprises at least one a polyol ester corresponding to the general formula (IIIb)

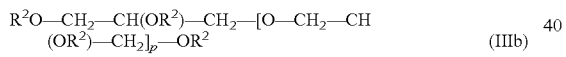

R²O—CH₂—CH(OR²)—CH₂—[O—CH₂—CH(OR²)—CH₂]ₚ—OR²   (IIIb)

wherein, in the general formula (IIIb),
the variable p represents an integer from 1 to 4,
R², independently of each other, represents: hydrogen, a radical CH₃—CH(OH)—CH₂—C(O)— or a radical CH₃—CH(OR¹)—CH₂—C(O)— with R¹=acyl group selected from an acetyl group of formula —C(O)—CH₃) and a propionyl group of formula —C(O)—C₂H₅, however, with the proviso that at least one radical R² represents a radical CH₃—CH(OH)—CH₂—C(O)— or a radical CH₃—CH(OR¹)—CH₂—C(O)— with R¹ as defined hereinabove.

14. The pharmaceutical composition according to claim 13,
wherein the pharmaceutical composition is a drug or a medicament.

15. The pharmaceutical composition according to claim 13,
wherein the pharmaceutical composition is a drug or a medicament for the treatment of a disease of the human body,
wherein the disease is selected from the group consisting of diseases associated with a disorder of the energy metabolism, diseases associated with a keto-body metabolism, craniocerebral trauma, stroke, hypoxia, cardiovascular diseases, myocardial infarction, refeeding syndrome, anorexia, epilepsy, neurodegenerative diseases, dementia, Alzheimer's disease, Parkinson's disease, multiple sclerosis, amyotrophic lateral sclerosis, fat metabolic diseases, glucose transporter defect (GLUT1 defect), VL-FAOD and mitochondriopathies, mitochondrial thiolase defect, Huntington's disease, cancers, T-cell lymphomas, astrocytomas and glioblastomas, HIV, rheumatic diseases, rheumatoid arthritis and arthritis urica, diseases of the gastrointestinal tract, chronic inflammatory bowel diseases, ulcerative colitis and Crohn's disease, lyosomal storage diseases, sphingolipidosis, Niemann-Pick disease, diabetes mellitus and effects or side-effects of chemotherapy.

16. A method of treating a human suffering from a disease,
wherein the method comprises a step of administering to said human an efficient dose of a pharmaceutical composition,
wherein the pharmaceutical composition comprises at least one a polyol ester corresponding to the general formula (IIIb)

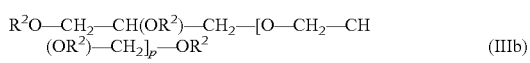

R²O—CH₂—CH(OR²)—CH₂—[O—CH₂—CH(OR²)—CH₂]ₚ—OR²   (IIIb)

wherein, in the general formula (IIIb),
the variable p represents an integer from 1 to 4,
R², independently of each other, represents: hydrogen, a radical CH₃—CH(OH)—CH₂—C(O)— or a radical CH₃—CH(OR¹)—CH₂—C(O)— with R¹=acyl group selected from an acetyl group of formula —C(O)—CH₃) or a propionyl group of formula —C(O)—C₂H₅, however, with the proviso that at least one radical R² represents a radical CH₃—CH(OH)—CH₂—C(O)— or a radical CH₃—CH(OR¹)—CH₂—C(O)— with R¹ as defined hereinabove.

17. The method according to claim 16,
wherein the disease is selected from the group consisting of diseases associated with a disorder of the energy metabolism, diseases associated with a keto-body metabolism, craniocerebral trauma, stroke, hypoxia, cardiovascular diseases, myocardial infarction, refeeding syndrome, anorexia, epilepsy, neurodegenerative diseases, dementia, Alzheimer's disease, Parkinson's disease, multiple sclerosis, amyotrophic lateral sclerosis, fat metabolic diseases, glucose transporter defect (GLUT1 defect), VL-FAOD and mitochondriopathies, mitochondrial thiolase defect, Huntington's disease, cancers, T-cell lymphomas, astrocytomas and glioblastomas, HIV, rheumatic diseases, rheumatoid arthritis and arthritis urica, diseases of the gastrointestinal tract, chronic inflammatory bowel diseases, ulcerative colitis and Crohn's disease, lyosomal storage diseases, sphingolipidosis, Niemann-Pick disease, diabetes mellitus and effects or side-effects of chemotherapy.

18. A food product,
wherein the food product comprises at least one a polyol ester corresponding to the general formula (IIIb)

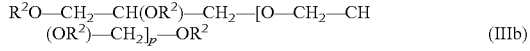

R²O—CH₂—CH(OR²)—CH₂—[O—CH₂—CH(OR²)—CH₂]ₚ—OR²   (IIIb)

wherein, in the general formula (IIIb),
the variable p represents an integer from 1 to 4,
R², independently of each other, represents: hydrogen, a radical CH₃—CH(OH)—CH₂—C(O)— or a radical CH₃—CH(OR¹)—CH₂—C(O)— with R¹=acyl group selected from an acetyl group of formula —C(O)—CH₃) or a propionyl group of formula —C(O)—C$_2$H$_5$, however, with the proviso that at least one radical R$^2$ represents a radical CH$_3$—CH(OH)—CH$_2$—C(O)— or a radical CH$_3$—CH(OR$^1$)—CH$_2$—C(O)— with R$^1$ as defined hereinabove.

19. The food product according to claim 18, wherein the food product is prepared for the application for catabolic metabolic states selected from the group consisting of hunger, diets and low-carbohydrate nutrition.

* * * * *